(12) United States Patent
Dutton

(10) Patent No.: US 8,846,619 B2
(45) Date of Patent: Sep. 30, 2014

(54) ARTIFICIAL OXYGEN TRANSPORT PROTEIN

(75) Inventor: P. Leslie Dutton, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 355 days.

(21) Appl. No.: 13/254,596

(22) PCT Filed: Mar. 4, 2010

(86) PCT No.: PCT/US2010/026248
§ 371 (c)(1),
(2), (4) Date: Nov. 17, 2011

(87) PCT Pub. No.: WO2010/102133
PCT Pub. Date: Sep. 10, 2010

(65) Prior Publication Data
US 2012/0065133 A1 Mar. 15, 2012

Related U.S. Application Data

(60) Provisional application No. 61/157,420, filed on Mar. 4, 2009.

(51) Int. Cl.
*A61K 38/00* (2006.01)
*A61P 7/00* (2006.01)
*C07K 14/805* (2006.01)

(52) U.S. Cl.
CPC .............. *C07K 14/805* (2013.01); *A61K 38/00* (2013.01)
USPC ........................................................ 514/13.5

(58) Field of Classification Search
None
See application file for complete search history.

(56) References Cited

U.S. PATENT DOCUMENTS

2007/0042439 A1  2/2007 Isogai et al.

FOREIGN PATENT DOCUMENTS

WO          94/15628         7/1994

OTHER PUBLICATIONS

Koder et al., "Design and engineering of an $O_2$ transport protein," Mar. 19, 2009, Nature, 458(7236):305-310.
International Search Report for PCT/US10/26248, dated Jul. 23, 2010.

*Primary Examiner* — Thomas Heard
(74) *Attorney, Agent, or Firm* — Saul Ewing, LLP; Kathryn Doyle

(57) ABSTRACT

This invention provides heme-containing peptides capable of binding molecular oxygen at room temperature. These compounds may be useful in the absorption of molecular oxygen from molecular oxygen-containing atmospheres. Also included in the invention are methods for treating an oxygen transport deficiency in a mammal.

19 Claims, 26 Drawing Sheets

Fig. 1

I. Assemble appropriate sized bundle

1     `abcdefg`
    `ELLKLLEELLKKLEELLKLLEELLKKL`

Generic 3-amino-acid sequence

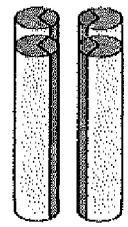

II. Insert cofactor-binding amino acids

2   `CGGG ELWKLHEELLKKFEELLKLHEERLKKL`

Constrain topology with loops; add W as spectroscopic tag;
add H to bind haem; break haem symmetry with R

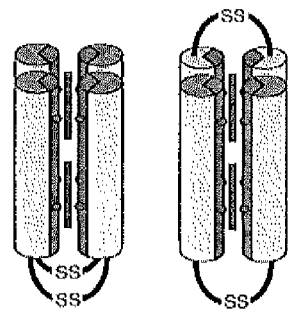

III. Improve structural resolution

3   `CGGG EIWKLHEEPLKKFEELLKLHEERLKKL`
    Pack apo core

4   `CGGG EIWKQHEEALKKFEEALKQFEE-LKKL`
    Remove excess haem sites; improve holo helical register 5   `CGGG EIWKQHEDALQKFEDALNQFEE-LKQL`
    Diversify surface residues to assist NMR analysis

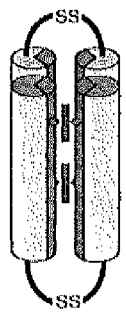

IV. Iteratively add and refine functions

6     `G EIWKQHEDALQKFEEALNQFED-LKQL GGSGCGSG`
      `G EIWKQHEDALQKFEEALNQFED-LKQL`

Link loops, constrain dynamics/water access

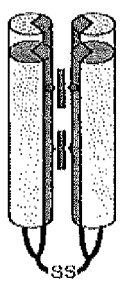

G EIWKQHEDALQKFEEALNQFED-LKQL GGSGCGSG
G EIWKQHEDALQKFEEALNQFED-LKQL
G EIWKQHEDALQKFEEALNQFED-LKQL GGSGCGSG
G EIWKQHEDALQKFEEALNQFED-LKQL

Meso

Deutero

Fig. 7

Construct 7
GMTPEQIWKQHEDALQKFEEALNQFEDLKQLGGSGSGSGG
EIWKQHEDALQKFEEALNQFEDLKQLGGSGGGSGG
EIWKQHEDALQKFEEALNQFEDLKQLGGSGSGSGG
EIWKQHEDALQKFEEALNQFEDLKQL Construct 8
GMTPEQIWKQHEDALQKFEEALNQFEDLKQLGGSGSGSGG
EIWKQHEDALQKFEEALNQFEDLKQLGGSGSGSGG
EIWKQHEDALQKFEEALNQFEDLKQLGGSGSGSGG
EIWKQHEDALQKFEEALNQFEDLKQL Construct 9
GEIWKQHEDALQKFEEALNQFEDLKQLGGSGSGSGG
EIWKQHEDALQKFEEALNQFEDLKQLGGSGSGSGG
EIWKQHEDALQKFEEALNQFEDLKQLGGSGSGSGG
EIWKQHEDALQKFEEALNQFEDLKQL

Fig. 8

| | | | |
|---|---|---|---|
| Construct 7 | 1 | GMTPE QWKQHEDALQKFEDALNQFEE-LKQL | GGSGSGSGG |
| | 2 | BWKQ HEDALQKFEDALNQFEE-LKQL | GGSGGGGSGG |
| | 3 | BWKQ HEDALQKFEDALNQFEE-LKQL | GGSGSGSGG |
| | 4 | BWKQ HEDALQKFEDALNQFEE-LKQL | |
| Construct 10 | 1 | GMTPE QWKQHEDALQKFEDALNQFEE-LKQL | GGSGSGSGG |
| | 2 | BCKCHEDALQKFEDALNQFEE-LKQL | GGSGGGGSGG |
| | 3 | BWKQ HEDALQKFEDALNQFEE-LKQL | GGSGSGSGG |
| | 4 | BWKQ HEDALQKFEDALNQFEE-LKQL | |
| Construct 8 | 1 | GMTPE QWKQHEDALQKFEDALNQFEE-LKQL | GGSGSGSGG |
| | 2 | BWKQ HEDALQKFEDALNQFEE-LKQL | GGSGSGSGG |
| | 3 | BWKQ HEDALQKFEDALNQFEE-LKQL | GGSGSGSGG |
| | 4 | BWKQ HEDALQKFEDALNQFEE-LKQL | |
| Construct 9 | 1 | G QWKQHEDALQKFEDALNQFEE-LKQL | GGSGSGSGG |
| | 2 | BWKQ HEDALQKFEDALNQFEE-LKQL | GGSGSGSGG |
| | 3 | BWKQ HEDALQKFEDALNQFEE-LKQL | GGGSGSGG |
| | 4 | BWKQ HEDALQKFEDALNQFEE-LKQL | |
| Construct 11 | 1 | MTPE QWKQHEDALQKFEALQFEDALNQFEE-LKQL | GGSGSGSGG |
| | 2 | BWKQ HEDALQKFEDALNQFEE-LKQL | GGSGGGGSGSGG |
| | 3 | BWKQ HEDALQKFEDALNQFEE-LKQL | GGSGCGSGG |
| | 4 | BWKQ HEDALQKFEALQFED-LKQL-NH$_2^*$ | |

Fig. 14

Construct 7:

MTPEQIWKQHEDALQKFEEALNQFEDLKQL GGSGSGSGG
EIWKQHEDALQKFEEALNQFEDLKQL GGSGGGSGG
EIWKQHEDALQKFEEALNQFEDLKQL GGSGSGSGG
EIWKQHEDALQKFEEALNQFEDLKQL

Construct 10:

MTPEQIWKQHEDALQKFEEALNQFEDLKQL GGSGSGSGG
ECIACHEDALQKFEEALNQFEDLKQL GGSGGGGSGG
EIWKQHEDALQKFEEALNQFEDLKQL GGSGSGSGG
EIWKQHEDALQKFEEALNQFEDLKQL

Fig. 15
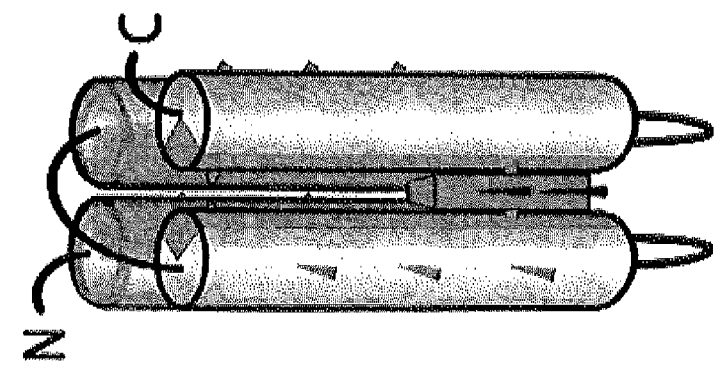
Construct 7
EIWKQHEDALQK
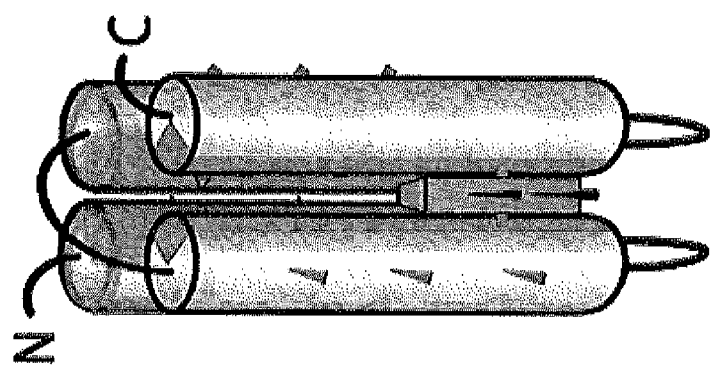
Construct 10
ECIACHEDALQK

Figure 16
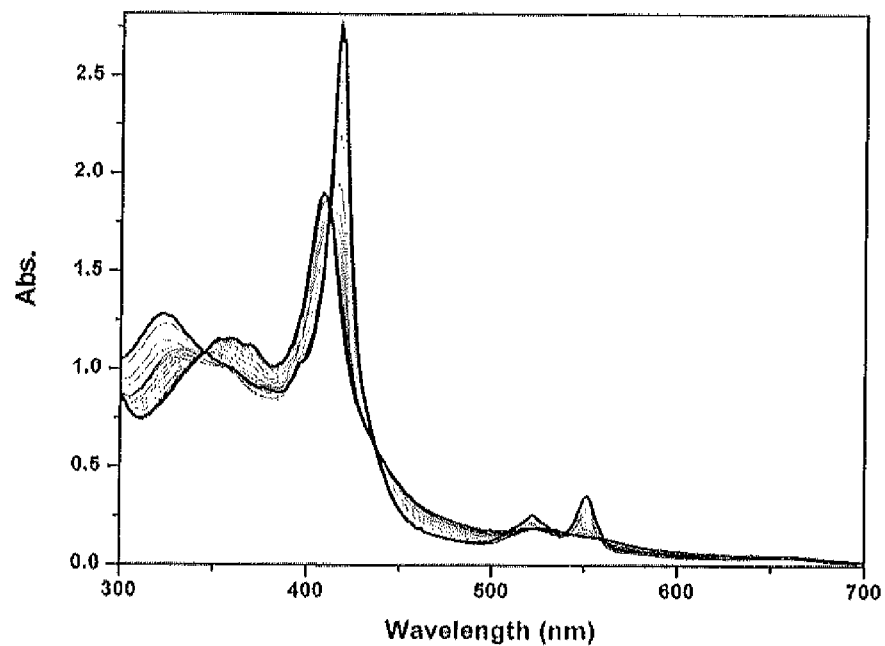
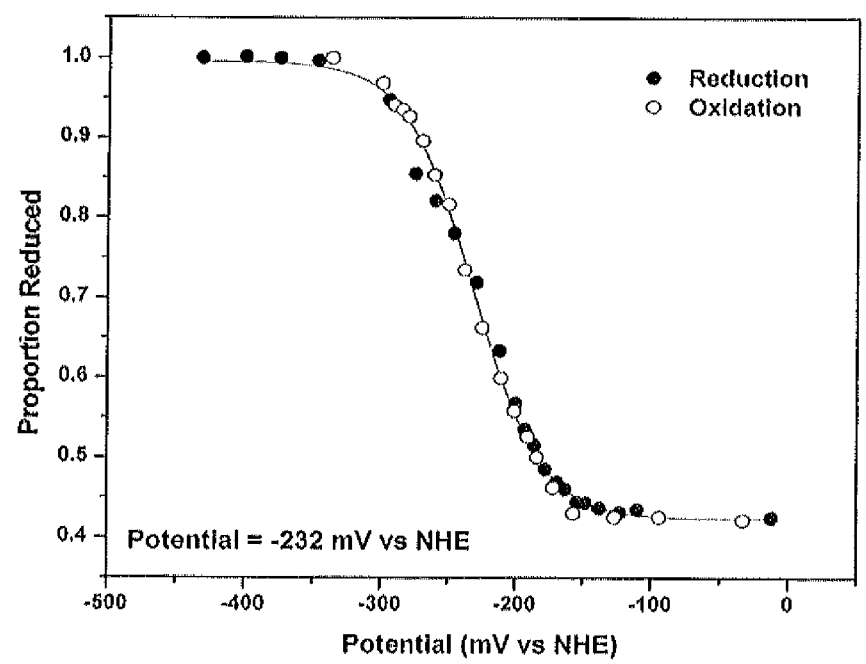

AP6:
C GGGEIWKQHEEALKKLFAFHFILPFIMAIAMVHLLFLFGEGL
C GGGEIWKQHEEALKKLFAFHFILPFIMAIAMVHLLFLFGEGL
C GGGEIWKQHEEALKKLFAFHFILPFIMAIAMVHLLFLFGEGL
C GGGEIWKQHEEALKKLFAFHFILPFIMAIAMVHLLFLFGEGL

ARTIFICIAL OXYGEN TRANSPORT PROTEIN

CROSS-REFERENCE TO RELATED APPLICATIONS

The present application is a 35 U.S.C. §371 national phase application from, and claiming priority to, International Application No. PCT/US2010/026248, filed Mar. 4, 2010, and published under PCT Article 21(2) in English, which claims priority to U.S. Provisional Application No. 61/157,410, filed Mar. 4, 2009, which applications are incorporated by reference herein in their entireties.

STATEMENT REGARDING FEDERALLY SPONSORED RESEARCH OR DEVELOPMENT

This invention was made with government support under grant number DOE-FG02-05-ER46223, awarded by the Department of Energy, grant number 2R01GM41048, awarded by the National Institutes of Health, and grant number DMR05-20020, awarded by the National Science Foundation. The government has certain rights in the invention.

BACKGROUND OF INVENTION

It has long been recognized that natural selection and evolution build complexity into natural proteins and biological systems [1-3]. This complexity frustrates biochemists seeking to understand structure and function [4], and presents an extraordinary challenge to protein engineers who aim to reproduce or create new functions in proteins. So far, this complexity has severely constrained the ability of protein engineers to approach the efficiency of natural protein catalysts [5-10]. No matter how common it may be in nature, complexity may in fact not be an essential feature of the proteins per se, nor may it be in fact an essential feature of catalysis, as shown by synthetic chemical systems [1,1]. By understanding the origins of complexity and attempting to separate multiple utilities and minimize complexity during the design and testing of artificial proteins that are completely independent of natural selection, it may be feasible to progressively build in sophisticated biochemical features that reproduce and exceed natural protein function.

Protein function requires more than a static structure [1,2]. In natural proteins, the motion that is part of engineering of protein function is often specific, which can make re-engineering motion for new functions prohibitively difficult. In contrast, artificial proteins offer a full palette of motions that can be edited to facilitate those that are productive and remove those that are unproductive.

Research efforts around protein design and engineering are driven by the great need to identify artificial proteins that are able to carry out functions once thought to be exclusive to naturally occurring proteins. Central targets in protein engineering are hemoglobin and related globins that are in charge of transporting molecular oxygen in the body. An artificial protein capable of performing hemoglobin's role in gas transport would find applications in boosting the blood's ability to carry oxygen gas and replacing depleted hemoglobin and/or red blood cells in patients. The present invention addresses this long-standing need.

SUMMARY OF THE INVENTION

In one aspect, the invention includes a peptide comprising an amino acid sequence selected from the group consisting of SEQ ID NO:1, the cystine derivative of SEQ ID NO:1, (SEQ ID NO:2)-LOOP-(SEQ ID NO:2), (SEQ ID NO:21)-LOOP-(SEQ ID NO:22)-LOOP-(SEQ ID NO:22)-LOOP-(SEQ ID NO:22), (SEQ ID NO:22)-LOOP-(SEQ ID NO:22)-LOOP-(SEQ ID NO:22)-LOOP-(SEQ ID NO:22), (SEQ ID NO:21)-LOOP-(SEQ ID NO:23)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:24), SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20.

In one embodiment, the peptide comprises an amino acid sequence selected from the group consisting of SEQ ID NO:1 and the cystine derivative of SEQ ID NO:1. In another embodiment, each occurrence of LOOP is independently selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGS-GCGSGG (SEQ ID NO:27). In yet another embodiment, the peptide comprises an amino acid sequence selected from the group consisting of (SEQ ID NO:2)-(SEQ ID NO:3)-(SEQ ID NO:2) and (SEQ ID NO:2)-(SEQ ID NO:4)-(SEQ ID NO:2). In yet another embodiment, the peptide comprises an amino acid sequence selected from the group consisting of SEQ ID NO:11, SEQ ID NO:12, SEQ ID NO:13, SEQ ID NO:14 and SEQ ID NO:15.

In another aspect, the invention includes a composition comprising: at least one heme; and a peptide comprising an amino acid sequence selected from the group consisting of SEQ ID NO:1, the cystine derivative of SEQ ID NO:1, (SEQ ID NO:2)-LOOP-(SEQ ID NO:2), (SEQ ID NO:21)-LOOP-(SEQ ID NO:22)-LOOP-(SEQ ID NO:22)-LOOP-(SEQ ID NO:22), (SEQ ID NO:22)-LOOP-(SEQ ID NO:22)-LOOP-(SEQ ID NO:22)-LOOP-(SEQ ID NO:22), (SEQ ID NO:21)-LOOP-(SEQ ID NO:23)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:24), SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20, wherein the peptide is bound to the at least one heme.

In one embodiment, the at least one heme is selected from the group consisting of heme A, heme B, heme C, heme O, mesohemes, deuterohemes, synthetic dicyano porphyrins and symmetrical porphyrins. In another embodiment, the at least one heme is heme C and the at least one heme is covalently bound to a cysteine residue of the peptide. In another embodiment, the peptide comprises an amino acid sequence selected from the group consisting of SEQ ID NO:1 and the cystine derivative of SEQ ID NO:1. In yet another embodiment, each occurrence of LOOP is independently selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGS-GCGSGG (SEQ ID NO:27). In yet another embodiment, the peptide comprises an amino acid sequence selected from the group consisting of (SEQ ID NO:2)-(SEQ ID NO:3)-(SEQ ID NO:2), and (SEQ ID NO:2)-(SEQ ID NO:4)-(SEQ ID NO:2). In yet another embodiment, the peptide comprises an amino acid sequence selected from the group consisting of SEQ ID NO:11, SEQ ID NO:12, SEQ ID NO:13, SEQ ID NO:14 and SEQ ID NO:15.

In yet another aspect, the invention includes a method of removing oxygen gas from an oxygen gas-containing atmosphere. The method comprises exposing to the oxygen gas-containing atmosphere a composition comprising: at least one heme; and a peptide comprising an amino acid sequence selected from the group consisting of SEQ ID NO:1, the cystine derivative of SEQ ID NO:1, (SEQ ID NO:2)-LOOP-(SEQ ID NO:2), (SEQ ID NO:22)-LOOP-(SEQ ID NO:22)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:22), (SEQ ID NO:21)-LOOP-(SEQ ID NO:23)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:24), SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20, wherein the at least one heme is bound to the peptide.

In one embodiment, the at least one heme is selected from the group consisting of heme A, heme B, heme C, heme O, mesohemes, deuterohemes, synthetic dicyano porphyrins and symmetrical porphyrins. In another embodiment, the at least one heme is heme C and the at least one heme is covalently bound to a cysteine residue of the peptide. In yet another embodiment, the peptide comprises an amino acid sequence selected from the group consisting of SEQ ID NO:1 and the cystine derivative of SEQ ID NO:1. In yet another embodiment, each occurrence of LOOP is independently selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGSGCGSGG (SEQ ID NO:27). In yet another embodiment, the peptide comprises an amino acid sequence selected from the group consisting of (SEQ ID NO:2)-(SEQ ID NO:3)-(SEQ ID NO:2), and (SEQ ID NO:2)-(SEQ ID NO:4)-(SEQ ID NO:2). In yet another embodiment, the peptide comprises an amino acid sequence selected from the group consisting of SEQ ID NO:11, SEQ ID NO:12, SEQ ID NO:13, SEQ ID NO:14 and SEQ ID NO:15.

In yet another aspect, the invention includes a method of treating an oxygen transport deficiency in a mammal in need thereof. The method comprises administering to the mammal an effective amount of a composition comprising: at least one heme; and a peptide comprising an amino acid sequence selected from the group consisting of SEQ ID NO:1, the cystine derivative of SEQ ID NO:1, (SEQ ID NO:2)-LOOP-(SEQ ID NO:2), (SEQ ID NO:21)-LOOP-(SEQ ID NO:22)-LOOP-(SEQ ID NO:22)-LOOP-(SEQ ID NO:22), (SEQ ID NO:22)-LOOP-(SEQ ID NO:22)-LOOP-(SEQ ID NO:22)-LOOP-(SEQ ID NO:22), (SEQ ID NO:21)-LOOP-(SEQ ID NO:23)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:24), SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20, wherein the at least one heme is bound to the peptide.

In one embodiment, the at least one heme is selected from the group consisting of heme A, heme B, heme C, heme O, mesohemes, deuterohemes, synthetic dicyano porphyrins and symmetrical porphyrins. In another embodiment, the at least one heme is heme C and the at least one heme is covalently bound to a cysteine residue of the peptide. In yet another embodiment, the peptide comprises an amino acid sequence selected from the group consisting of SEQ ID NO:1 and the cystine derivative of SEQ ID NO:1. In yet another embodiment, each occurrence of LOOP is independently selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGSGCGSGG (SEQ ID NO:27). In yet another embodiment, the peptide comprises an amino acid sequence selected from the group consisting of (SEQ ID NO:2)-(SEQ ID NO:3)-(SEQ ID NO:2), and (SEQ ID NO:2)-(SEQ ID NO:4)-(SEQ ID NO:2). In yet another embodiment, the peptide comprises an amino acid sequence selected from the group consisting of SEQ ID NO:11, SEQ ID NO:12, SEQ ID NO:13, SEQ ID NO:14 and SEQ ID NO:15. In yet another embodiment, the oxygen transport deficiency is selected from the group consisting of chronic anemia, acute anemia, sickle cell anemia, anemia associated with cancer, anemia associated with cancer chemotherapy, and anemia associated with use of radiation for cancer treatment. In yet another embodiment, the mammal is human.

In yet another aspect, the invention includes a preparation comprising a vesicle. The vesicle comprises an amphiphilic material which is selected from the group consisting of a detergent, a phospholipid, and a combination thereof; at least one heme; and a peptide comprising an amino acid sequence selected from the group consisting of SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20, wherein the peptide is incorporated in the walls of the vesicle and the peptide is bound to the at least one heme.

In one embodiment, the at least one heme is selected from the group consisting of heme A, heme B, heme C, heme O, mesohemes, deuterohemes, synthetic dicyano porphyrins and symmetrical porphyrins.

In yet another aspect, the invention includes a method of treating an oxygen transport deficiency in a mammal in need thereof. The method comprises administering to the mammal an effective amount of a composition comprising a vesicle. The vesicle comprises: an amphiphilic material which is selected from the group consisting of a detergent, a phospholipid, and a combination thereof; at least one heme; and a peptide comprising an amino acid sequence selected from the group consisting of SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20, wherein the peptide is incorporated in the walls of the vesicle and the peptide is bound at the at least one heme.

In one embodiment, the at least one heme is selected from the group consisting of heme A, heme B, heme C, heme O, mesohemes, deuterohemes, synthetic dicyano porphyrins and symmetrical porphyrins. In another embodiment, the oxygen transport deficiency is selected from the group consisting of chronic anemia, acute anemia, sickle cell anemia, anemia associated with cancer, anemia associated with cancer chemotherapy, and anemia associated with use of radiation for cancer treatment. In yet another embodiment, the mammal is human.

DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 illustrates the design of an artificial oxygen transport protein (Construct numbers are identified on the left side of the drawing). The design starts from the simple heptad near-repeat sequence using just three amino acids (Construct 1). Boxes around amino acid sequences highlight heptad divisions, and key steps in the design process are shown. In Constructs 2-5, helical sequences shown are dimerized as cysteine disulfide loops (cystine loops) and self-assemble in four-helix bundles. In Construct 6, a longer loop (underlined) unites two identical sequences, with the loops themselves now disulfide-linked, as shown schematically to the right. Construct 1 corresponds to SEQ ID NO:5. Construct 2 corresponds to the cystine derivative of SEQ ID NO:6. Construct 3 corresponds to the cystine derivative of SEQ ID NO:7. Construct 4 corresponds to the cystine derivative of SEQ ID NO:8. Construct 5 corresponds to the cystine derivative of SEQ ID NO:9. Construct 6 corresponds to the cystine derivative of SEQ ID NO:1.

FIGS. 2A-2D, illustrates spectra for the Constructs of the invention. FIGS. 2A and 2B represent data collected at −15° C. for the following species: oxidized, reduced, carboxy-ferrous or oxy-ferrous forms of Construct 6 with either heme B (FIG. 2A) or heme A (FIG. 2B) as the cofactor. Panels C and D represent stopped-flow spectral changes for mixing the reduced heme B proteins with oxygen at 15° C. The fully designed oxygen transport protein Construct 6 (FIG. 2C) showed the transformation of the reduced heme to the oxy-ferrous state (marked by an asterisk), which eventually became oxidized. In the case of Construct 2 (FIG. 2D), the reaction proceeded directly and rapidly to the oxidized form.

FIG. 3, comprising In FIG. 3A, each helix is represented by a circle, and each quartet of circles represents a four-helix bundle. For each four-helix bundle, the two circles on top are the N-terminus ends of the helices, and the two circles on bottom are the C-terminus ends of the helices. Heme binding rotates helices but incurs strain by burying glutamates (triangles). Like some natural hemoglobins, at least two conformations are present, with the closed form not being able to bind CO. Histidine (His) release with helical rotation precedes gaseous ligand binding. As illustrated in FIG. 3B, immediate CO photolysis difference spectra (4-0 µs) of Construct 6 heme B was followed by a rapid microsecond relaxation (32-4 µs), followed by slower histidine and CO binding (2-0.5 ms, shown in 3×) and even slower displacement of histidine by CO (2-0 ms). FIG. 3C illustrates subsequent biphasic recombination kinetics (characteristic times $t_1$ and $t_2$) at 418 nm. As illustrated in FIG. 3D, the product (top graph) and sum (bottom graph) of these characteristic times as a function of CO concentration may be used to determine histidine on/off rates.

FIG. 6, comprising FIG. 6C illustrates the approximate % oxyferrous species for Construct 6 complexed with mesoheme and deuteroheme.

FIG. 7 illustrates the amino acid sequence of Constructs 7-9. Construct 7 corresponds to SEQ ID NO:11. Construct 8 corresponds to SEQ ID NO:12. Construct 9 corresponds to SEQ ID NO:13.

FIG. 8 illustrates the amino acid sequence of Constructs 7-11. Construct 7 corresponds to SEQ ID NO:11. Construct 8 corresponds to SEQ ID NO:12. Construct 9 corresponds to SEQ ID NO:13. Construct 10 corresponds to SEQ ID NO:14, Construct 11 corresponds to SEQ ID NO:15.

FIG. 14 illustrates the amino acid sequence of Constructs 7 (which corresponds to SEQ ID NO:11) and 10 (which corresponds to SEQ ID NO:14). The CXXCH insertion sequence is underlined in Construct 10.

FIG. 15 is a schematic diagram of the structure of Constructs 7 (which corresponds to SEQ ID NO:11) and 10 (which corresponds to SEQ ID NO:14). Sequences EIWKQHEDALQK (SEQ ID NO:28) and ECIACHED-ALQK (SEQ ID NO:29) are illustrated.

FIG. 16, comprising FIGS. 16A-B, illustrates potentiometry data for Construct 10. Spectra acquired during potentiometry of Construct 10 (FIG. 16A) showed classic c-type heme responses and reversible one-electron Nernst redox behavior (right) with an $E_m$ of −232 mV, slightly more positive than b-hemes in similar constructs.

FIGS. 17A-C, illustrates the formation of oxy-ferrous Construct 10 in a stopped flow experiment. Soret peak (FIG. 17A) and alpha-beta band (FIG. 17B) absorbance spectra indicated four forms of Construct 10. Reduced, oxidized and oxy were determined by SVD analysis on full spectral kinetic data from the experiment and match literature spectra for the species. Carboxy was determined in a separate experiment. Kinetic trace (FIG. 17C) suggests auto-oxidation of oxy-ferrous heme.

FIGS. 23A-C, illustrates AP6 and its binding to $O_2$. FIG. 23A is a schematic representation of AP6 in detergent. FIG. 23B is a schematic representation of AP6a in a membrane. FIG. 23C is a series of UV-vis spectra of AP6a in different $O_2$-binding states. (1) corresponds to ferrous heme, no $O_2$. (2) corresponds to ferrous heme, $O_2$ state. (3) corresponds to ferric heme, no $O_2$.

DETAILED DESCRIPTION OF INVENTION

Figure 2:
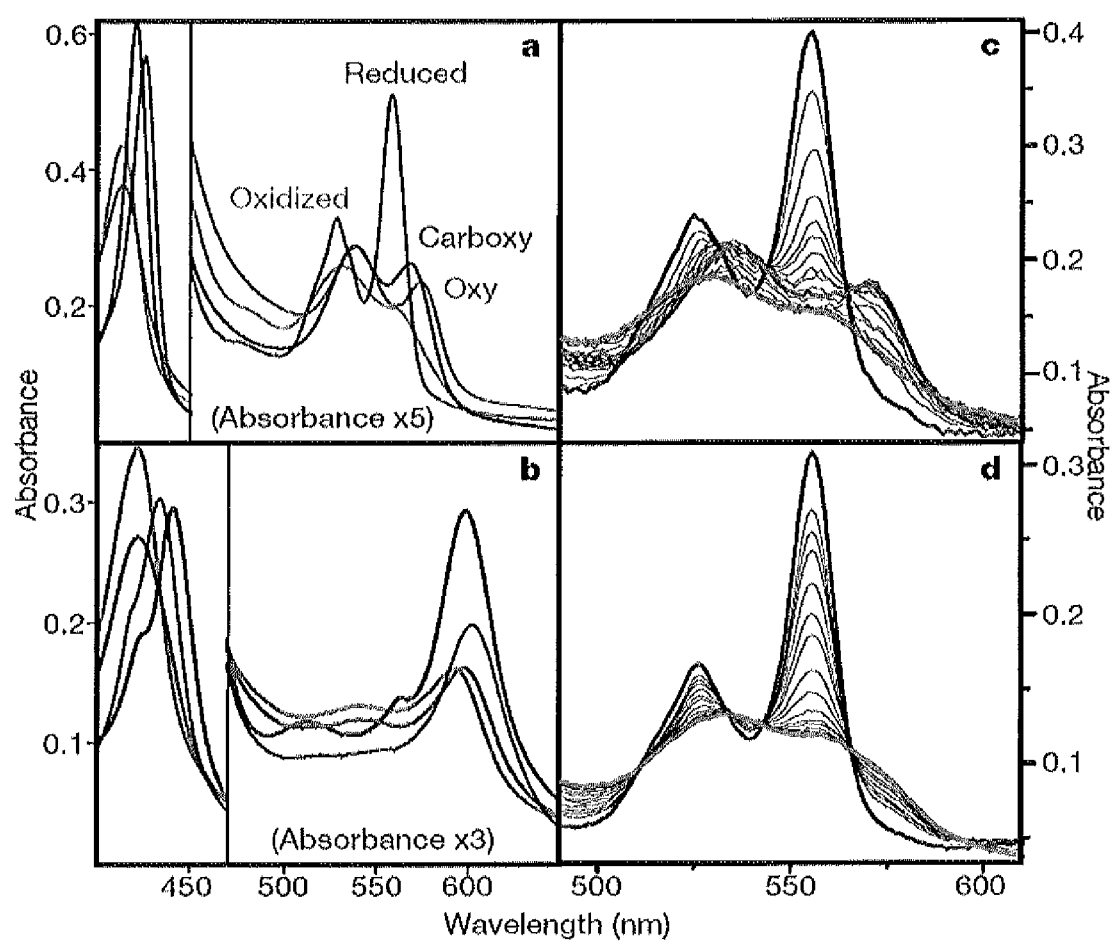
FIG. 2, comprising

As described herein, the invention includes heme-containing peptides that are capable of binding molecular oxygen stably at room temperature. Heme-containing peptides that bind to molecular oxygen more tightly than carbon monoxide are also included in the invention. The heme-containing peptides and analogs thereof are useful in absorbing molecular oxygen from molecular oxygen-containing environments. The heme-containing peptides and analogs thereof are also useful in treating a disease associated with deficient molecular oxygen transport in a patient in need thereof. The heme-containing peptides and analogs thereof are further useful for the preparation of a non-antigenically active $O_2$-binding protein delivery system.

DEFINITIONS

The definitions used in this application are for illustrative purposes and do not limit the scope used in the practice of the invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

As used herein, the articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic will have a N-terminus and a C-terminus. The N-terminus will have an amino group, which can be free (i.e., as a $NH_2$ group) or appropriately protected (for example, with a BOC or a Fmoc group). The C-terminus will have a carboxylic group, which can be free (i.e., as a COOH group) or appropriately protected (for example, as a benzyl or a methyl ester). A cyclic peptide does not necessarily have free N- or C-terminii, since they are covalently bonded through an amide bond to form the cyclic structure.

As used herein, amino acids are represented by the full name thereof, by the three-letter code, as well as the one-letter code corresponding thereto, as indicated in the following table. The structure of amino acids and their abbreviations can also be found in the chemical literature, such as in Stryer, 1988, "Biochemistry", $3^{rd}$ Ed., W. H. Freeman and Co., New York.

| Full Name | Three-Letter Code | One-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "cystine derivative" of a peptide that contains at least one cysteine residue refers to a double-chain peptide formed by the reaction of two identical chains of the peptide wherein each contains a cysteine residue, wherein the cysteine residue of one chain reacts with the cysteine residue of the other chain to form a cystine. When the starting peptide has one single cysteine residue, there is only one possible cystine derivative of the peptide. When the starting peptide has more than one cysteine residues, more than one cystine derivatives of the peptide may be formed, depending on the protection status of the various cysteine residues at the time of the dimerization reaction.

As used herein, the term "(SEQ ID NO:X)-(SEQ ID NO:Y)" indicates that SEQ ID NO:X is covalently linked to SEQ ID NO:Y by an amide bond, involving the carboxylate group on the C-terminus of SEQ ID NO:X and the amino group on the N-terminus of SEQ ID NO:Y. Accordingly, the term "(SEQ ID NO:X)-LOOP-(SEQ ID NO:Y)" indicates that SEQ ID NO:X is covalently linked to LOOP by an amide bond, involving the carboxylate group on the C-terminus of SEQ ID NO:X and an amino group in LOOP, and LOOP is covalently linked to SEQ ID NO:Y by an amide bond, involving a carboxylate group in LOOP and the amino group in the N-terminus of SEQ ID NO:Y.

As used herein, the term "LOOP" refers to a chemical linker that connects two protein segments and is able to form a loop between the two protein segments. In one embodiment, LOOP is a peptide of 6 to 15 amino acid residues, a hydrocarbon chain of 18 to 30 carbons, or a chain consisting of $-HN^{-1}(CH_2CH_2O)_nCH_2C(O)-$, wherein "n" is an integer of value between 5 and 10, the group —HN$_1$ forms an amide bond with the carboxylate group at the C-terminus of one protein segment and CH$_2$C(O)— forms an amide bond with the amino group at the N-terminus of the other protein segment. In another embodiment, LOOP is a peptide consisting of from 6 to 15 amino acids. In another embodiment, LOOP is a peptide consisting of from 8 to 11 amino acids. In yet another embodiment, LOOP is a peptide formed by amino acids selected from the group of glycine, serine and cysteine. In yet another embodiment, LOOP is a peptide of amino acid sequence selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGSGCGSGG (SEQ ID NO:27).

As used herein, the term "heme" refers to a prosthetic group formed of an iron atom contained in the center of a large heterocyclic organic ring called a porphyrin. Not all porphyrins contain iron, but a substantial fraction of porphyrin-containing metalloproteins have heme as their prosthetic subunit; these are known as hemoproteins. Non-limiting examples of hemes are heme A, heme B, heme C, heme O, mesohemes, deuterohemes, synthetic dicyano porphyrins and symmetrical porphyrins (such as, but not limited to, protoporphyrin III).

As used herein to refer to the association between heme and the peptides of the invention, the term "bound" indicates that the heme is coordinated to residues of the peptide, forming a complex. The complex may be more or less labile, depending on the specific nature of the heme and the peptide in use. In one embodiment, the complex between the heme and the peptides is stable enough for the complex to be useful within the needs of the invention. In another embodiment, the heme is covalently bound to the peptides of the invention.

As used herein with respect to the compounds of the invention, "biologically active" means that the compounds elicit a biological response in a mammal that can be monitored and characterized in comparison with an untreated mammal. One possible biological response within the invention relates to the ability of the compound to avoid, reduce or treat an oxygen transport deficiency in a mammal. In this particular case, the compound is administered to the mammal orally, nasally, rectally, intravaginally, parenterally, buccally, sublingually, intragastrically or topically. The mammal and the level of oxygen gas in its body are monitored as a function of time, and the observation of a measurable and dose-dependent change in level of oxygen gas in its body (especially in the blood stream) is evidence that the compound displays biological activity. This preferred biological response does not limit or restrict the disclosures or embodiments of the invention in any way.

As used herein, the term "oxygen transport deficiency" corresponds to a disease, condition or ailment characterized by lower than normal levels of oxygen in tissues or blood stream. Non-limiting examples of oxygen transport deficiencies are chronic or acute anemia, conditions associated with malfunctioning hemoglobin (such as sickle cell anemia), and conditions associated with inappropriate amount of circulating hemoglobin and/or red blood cells (such as anemias associated with cancer, with use of cancer chemotherapy, with use of radiation for cancer treatment or with considerable loss of blood due to injury or surgery).

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein, a "subject" or a "mammal" includes a human or a non-human mammal Non-human mammals include, for example, livestock and pets, such as ovine, bovine, porcine, canine, feline and murine mammals. Preferably, the subject or mammal is canine, feline or human. Most preferably, the subject or mammal is human.

As used herein, the language "effective amount" or "therapeutically effective amount" refers to a non-toxic but sufficient amount of the composition used in the practice of the invention that is effective to level, moderate or increase the level of oxygen gas in the body of a mammal. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein, a "prophylactic" or "preventive" treatment is a treatment administered to a subject who does not exhibit signs of a disease or disorder or exhibits only early signs of the disease or disorder for the purpose of decreasing the risk of developing pathology associated with the disease or disorder.

As used herein, a "therapeutic" treatment is a treatment administered to a subject who exhibits signs of pathology of a disease or disorder for the purpose of diminishing or eliminating those signs.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. As used herein "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds can also be incorporated into the compositions.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., treating, ameliorating, or preventing shivering in a subject.

"Applicator," as the term is used herein, is used to identify any device including, but not limited to, a hypodermic syringe, a pipette, and the like, for administering the compounds and compositions used in the practice of the invention.

Peptides of the Invention

The invention includes a peptide comprising the amino acid sequence of SEQ ID NO:1, represented below:
GEIWKQHEDALQKFEEALNQFEDLKQLGGSG
CGSGGEIWKQHEDALQKFEE ALNQFEDLKQL. In this representation, the cysteine residue (residue 42) is underlined for clarity.

The invention also includes a peptide comprising the amino acid sequence of the cystine derivative of SEQ ID NO:1, shown below:

The invention also includes a peptide comprising an amino acid sequence selected from the group consisting of (SEQ ID NO:21)-LOOP-(SEQ ID NO:22)-LOOP-(SEQ ID NO:22)-LOOP-(SEQ ID NO:22), (SEQ ID NO:22)-LOOP-(SEQ ID NO:22)-LOOP-(SEQ ID NO:22)-LOOP-(SEQ ID NO:22), (SEQ ID NO:21)-LOOP-(SEQ ID NO:23)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:24), SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20. In one embodiment, LOOP is selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGSGCGSGG (SEQ ID NO:27).

Compositions of the Invention

The invention includes a composition comprising at least one heme, and a peptide comprising an amino acid sequence selected from the group consisting of SEQ ID NO:1, the cystine derivative of SEQ ID NO:1, (SEQ ID NO:2)-LOOP-(SEQ ID NO:2), (SEQ ID NO:22)-LOOP-(SEQ ID NO:22)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:22), (SEQ ID NO:21)-LOOP-(SEQ ID NO:23)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:24), SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20, wherein the peptide is bound to the at least one heme. The heme may be bound to

```
                    Cystine Derivative of SEQ ID NO: 1
GEIWKQHEDALQKFEEALNQFEDLKQLGGSGCGSGGEIWKQHEDALQKFEEALNQFEDLKQL
                               |
GEIWKQHEDALQKFEEALNQFEDLKQLGGSGCGSGGEIWKQHEDALQKFEEALNQFEDLKQL
```

The cystine derivative of SEQ ID NO:1 may be prepared by the dimerization of the peptide of the amino acid sequence of SEQ ID NO:1, wherein the cysteine residues (residue 42), one from each monomeric chain, react to form a cystine bond. This reaction consists of a net oxidation of the cysteine residue to a cystine residue and may be achieved by exposing the peptide of amino acid of SEQ ID NO:1 to air or chemical reagents known to oxidize cysteine residues to cystine residues. By the same principle, a peptide comprising the amino acid sequence of cystine derivative of SEQ ID NO:1 may be prepared by the dimerization of a peptide comprising the amino acid sequence of SEQ ID NO:1. Analogously, other cystine derivatives of the invention may be prepared from the corresponding cysteine-containing peptides of the invention using the protocol described above.

The invention further includes a peptide comprising the amino acid sequence of (SEQ ID NO:2)-LOOP-(SEQ ID NO:2), wherein SEQ ID NO:2 is GEIWKQHEDALQKFEEALNQFEDLKQL. In one embodiment, LOOP is GGSGSGSG or GGSGGGSG. In yet another embodiment, the peptide of the invention comprises the amino acid sequence selected from the group consisting of (SEQ ID NO:2)-(SEQ ID NO:3)-(SEQ ID NO:2) and (SEQ ID NO:2)-(SEQ ID NO:4)-(SEQ ID NO:2).

the peptide through covalent or non-covalent bonds. In an embodiment, the heme is covalently bound to a cysteine residue of the peptide. In an embodiment, the heme is selected from the group consisting of heme A, heme B, heme C, heme O, mesohemes, deuterohemes, synthetic dicyano porphyrins and symmetrical porphyrins. In another embodiment, each instance of LOOP is independently selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGSGCGSGG (SEQ ID NO:27). The composition may further comprise a pharmaceutically acceptable carrier.

The invention also includes a preparation comprising a vesicle. The vesicle comprises an amphiphilic material, at least one heme, and a peptide comprising an amino acid sequence selected from the group consisting of SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20. In one aspect, the peptide of the invention is incorporated in the walls of the vesicle, whereby the outer residues of the peptide structure contact the molecules that comprises the vesicle wall.

The amphiphilic material used in the preparation of the vesicle may be a detergent, a phospholipid or a mixture thereof. The detergent useful within the invention may be an anionic detergent, a cationic detergent, a zwitterion ionic detergent and a non-ionic detergent. Non-limiting examples of ionic detergents are perfluorooctanoate, perfluorooctanesulfonate, sodium dodecyl sulfate (SDS), ammonium lauryl sulfate, and other alkyl sulfate salts, sodium laureth sulfate, also known as sodium lauryl ether sulfate (SLES), alkyl benzene sulfonate, soaps and fatty acid salts. Non-limiting examples of cationic detergents are cetyl trimethylammonium bromide (CTAB), also known as hexadecyl trimethyl ammonium bromide, and other alkyltrimethylammonium salts, cetylpyridinium chloride (CPC), polyethoxylated tallow amine (POEA), benzalkonium chloride (BAC), and benzethonium chloride (BZT). Non-limiting examples of zwitterionic (amphoteric) detergents are dodecyl betaine, cocamidopropyl betaine and coco ampho glycinate. Non-limiting examples of non-ionic detergents are alkyl poly(ethylene oxide), alkylphenol poly(ethylene oxide), copolymers of poly(ethylene oxide) and poly(propylene oxide) (commercially called Poloxamers or Poloxamines), alkyl polyglucosides (including octyl glucoside and decyl maltoside), fatty alcohols (including cetyl alcohol and oleyl alcohol), cocamide MEA, cocamide DEA, polysorbates (such as Tween 20, Tween 80 and dodecyl dimethylamine oxide).

The phospholipid useful within the invention may be a diacylglyceride, such as phosphatidic acid (phosphatidate), phosphatidylethanolamine (cephalin), phosphatidylcholine (lecithin), phosphatidylserine, sphingomyelin or phosphoinositides. Non-limiting examples of phosphoinositides are phosphatidylinositol, phosphatidylinositol phosphate, phosphatidylinositol bisphosphate and phosphatidylinositol triphosphate.

Methods of the Invention

The invention includes a method of removing oxygen gas from an oxygen gas-containing atmosphere. The method comprises exposing to the oxygen gas-containing atmosphere a composition comprising at least one heme and a peptide of the invention, wherein the peptide of the invention is bound to the at least one heme.

In a non-limiting aspect, oxygen gas binds to the heme which is bound to the peptide of the invention, and as a result the oxygen gas is removed from the atmosphere. In one embodiment, the binding of the oxygen gas to the composition of the invention is reversible. In another embodiment, the binding of the oxygen gas to the composition of the invention is irreversible.

The invention also includes a method of treating an oxygen transport deficiency in a mammal. The method comprises administering to the mammal in need thereof an effective amount of a composition comprising at least one heme bound to a peptide of the invention. In one aspect, the peptide-bound heme is able to deliver oxygen to the tissues that have lower oxygen levels than the oxygen gas levels generally accepted as normal or healthy by medical specialists. In another aspect, the peptide-bound heme is able to remove oxygen to the tissues that have an overall excess level of oxygen gas compared to the oxygen gas levels generally accepted as normal or healthy by medical specialists. In another aspect, the method of the invention is useful for treating an oxygen transport deficiency selected from the group consisting of chronic anemia, acute anemia, sickle cell anemia, anemia associated with cancer, anemia associated with cancer chemotherapy, and anemia associated with use of radiation for cancer treatment. In another aspect, the mammal is human.

The invention further includes a method of treating an oxygen transport deficiency in a mammal. The method comprises administering to the mammal an effective amount of a composition comprising a vesicle, wherein the vesicle comprises an amphiphilic material, at least one heme, and a peptide of the invention with an amino sequence selected from the group consisting of SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20. The peptide useful within this method binds to the at least one heme. The amphiphilic material may be a detergent, a phospholipid or a mixture thereof.

In one aspect, the heme-peptide complex may bind $O_2$ and deliver it to tissues that have lower than optimal concentrations of $O_2$. In another aspect, the heme-peptide complex may bind $O_2$ and remove it from tissues that have higher than optimal concentrations of $O_2$ Therapeutic Use and Pharmaceutical Compositions The compositions of the invention are useful for treatment of an oxygen transport deficiency. One skilled in the art can readily determine an effective amount of composition to be administered to a subject, by taking into account factors such as the size and weight of the subject; the extent of the oxygen transport deficiency observed in the subject; the age, health and sex of the subject; the route of administration; and whether the administration is local or systemic. Generally, the amount of composition to be administered depends upon the degree of the oxygen transport deficiency, and the biological activity exhibited by the compounds of the invention. Those skilled in the art may derive appropriate dosages and schedules of administration to suit the specific circumstances and needs of the subject. For example, suitable doses of compounds of the invention to be administered may be between about 0.014 mg/kg and about 72 mg/kg body weight. In some embodiments, dosages are between about 0.14 mg/kg and about 24 mg/kg body weight.

It is understood that the effective dosage will depend on the age, sex, health, and weight of the recipient, kind of concurrent treatment, if any, frequency of treatment, and the nature of the effect desired. The most preferred dosage will be tailored to the individual subject, as is understood and determinable by one of skill in the art, without undue experimentation.

A mixture of two or more compounds of the invention can be administered in equimolar concentrations to a subject in need of such treatment. Alternatively, two or more compounds of the invention are administered in concentrations that are not equimolar. In yet other instances, two or more of the compounds of the invention may be administered in equal concentrations or equal weights per kilogram of body weight. For example, the compounds may be administered in equal amounts, based on the weight of the subject. In another instance, the compounds of the invention may be administered in unequal amounts. In yet other instances, the amount of each compound of the invention to be administered is based on its biological activity.

In general, the schedule or timing of administration of a mixture of compounds is according to the accepted practice for the procedure being performed.

When used in vivo, the compounds of the invention are preferably administered as a pharmaceutical composition, comprising a mixture, and a pharmaceutically acceptable carrier. The compounds of the invention may be present in a pharmaceutical composition in an amount from 0.001 to 99.9 wt %, more preferably from about 0.01 to 99 wt %, and even more preferably from 0.1 to 95 wt %.

All of the various compounds of the invention to be administered need not be administered together in a single composition. The different compounds may be administered in separate compositions. For example, if three different compounds of the invention are to be administered, the three different compounds may be delivered in three separate compositions. In addition, each compound may be delivered at the same time, or the compounds may be delivered consecutively with respect to one another. Thus, the mixture of the compounds may be administered in a single composition, or in multiple compositions comprising one or more compounds of the invention.

The regimen of administration may affect what constitutes an effective amount. For example, the therapeutic formulations may be administered to the mammal either prior to or after the onset of an oxygen transport deficiency event in the mammal. Further, several divided dosages, as well as several staggered dosages, may be administered daily or sequentially, or the dose may be continuously infused, or can be a bolus injection. Further, the dosages of the therapeutic formulations may be proportionally increased or decreased as indicated by the exigencies of the therapeutic or prophylactic situation.

In particular embodiments, it is especially advantageous to formulate compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specifications for the dosage unit forms of the invention are dictated by and directly dependent on: (a) the unique characteristics of the therapeutic compound and the particular therapeutic effect to be achieved, and (b) the limitations inherent in the art of compounding/formulating such a therapeutic compound for the treatment of shivering or temperature spiking in a mammal.

In view of the disclosure contained herein, those skilled in the art will appreciate that the present compositions are capable of having a beneficial effect in a variety of surgical interventions, such as, but not limited to, general surgery, cosmetic surgery, neurosurgical procedures, cardiovascular procedures, organ amputations, and oncology-related interventions. It is therefore contemplated that the compositions of this invention may take numerous and varied forms, depending upon the particular circumstance of each application. For example, the compositions of the invention may be incorporated into a solid pill or may in the form of a liquid dispersion or suspension. In general, therefore, the compositions of the present invention preferably comprise a peptide of the invention and a suitable, non-toxic, physiologically acceptable carrier. As the term is used herein, "carrier" refers broadly to materials that facilitate administration or use of the present compositions for treatment of oxygen transport deficiency in surgical interventions. A variety of non-toxic physiologically acceptable carriers may be used in forming these compositions, and it is generally preferred that these compositions be of physiologic salinity.

For some applications involving treatment of an oxygen transport deficiency in the broadest sense, it is desirable to have available a physically applicable or implantable predetermined solid form of material containing the composition of the invention. In such embodiments, the compositions of the present invention are preferably combined with a solid carrier that itself is bio-acceptable and suitably shaped for its use.

The compositions of the invention may be administered using any method designed to allow compounds to have a physiological effect. Administration may be enterally or parenterally; for example orally, rectally, intracisternally, intravaginally, intraperitoneally or locally. Parenteral administrations are preferred.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques. Particularly preferred parenteral administration methods include intravascular administration (e.g., intravenous bolus injection, intravenous infusion, intra-arterial bolus injection, intra-arterial infusion and catheter instillation into the vasculature), peri- and intratarget tissue injection, subcutaneous injection or deposition including subcutaneous infusion (such as by osmotic pumps), intramuscular injection, intraperitoneal injection, and direct application to the target area, for example by a catheter or other placement device.

The compositions of the invention are useful for prophylactic and/or therapeutic treatment of the relevant disease condition. The pharmaceutical compositions can be administered in a variety of unit dosage forms depending upon the method of administration.

The pharmaceutical compositions of this invention are particularly useful for parenteral administration, such as administration into a body cavity or lumen of an organ. The compositions for administration will commonly comprise a solution or suspension of the compound in a pharmaceutically acceptable carrier, preferably an aqueous carrier. A variety of aqueous carriers can be used, e.g., buffered saline and the like. These suspensions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The amount of the compound may vary widely, and will be selected primarily based on fluid volumes, viscosities, body weight and the like in accordance with the particular mode of administration selected and the subject's needs.

Thus, a typical pharmaceutical composition for intravenous administration would be about 1 mg to 5,000 mg per subject per day. Dosages from 1 up to about 3,000 mg per subject per day may be used, particularly when the drug is administered to a secluded site and not into the blood stream, such as into a body cavity or into a lumen of an organ. Methods for preparing parenterally administrable compositions will be known or apparent to those skilled in the art and are described in more detail in such publications as Remington's Pharmaceutical Science, 15th ed., 1980, Mack Publishing Company, Easton (PA).

The compositions containing the compound of the invention may be administered for therapeutic treatments. In therapeutic applications, preferred pharmaceutical compositions are administered in a dosage sufficient to treat an oxygen transport deficiency. An amount adequate to accomplish this is defined as a "therapeutically effective dose." Amounts effective for this use will depend upon the severity of the disease and the general state of the subject's health.

Single or multiple administrations of the compositions may be administered depending on the dosage and frequency as required and tolerated by the subject. In any event, the administration regime should provide a sufficient quantity of the composition of this invention to treat the subject effectively.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Pharmaceutical compositions that are useful in the methods used in the practice of the invention may be prepared, packaged, or sold in formulations suitable for oral, rectal, intracisternal, intravaginal, intraperitoneal or local, or another route of administration. Other contemplated formulations include projected nanoparticles, liposomal preparations, resealed erythrocytes containing the active ingredient, and immunologically-based formulations.

A pharmaceutical composition used in the practice of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition used in the practice of the invention will vary, depending upon the identity, size, and condition of the subject treated and further depending upon the route by which the composition is to be administered. By way of example, the composition may comprise between 0.01% and 99.9% (w/w) active ingredient.

Controlled- or sustained-release formulations of a pharmaceutical composition used in the practice of the invention may be made using conventional technology.

A formulation of a pharmaceutical composition used in the practice of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid comprises a carbon-containing liquid molecule that exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition used in the practice of the invention that are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropyl methylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Powdered and granular formulations of a pharmaceutical preparation used in the practice of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition used in the practice of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (e.g. such as with a physiologically degradable material), and methods of absorbing an aqueous or oily solution or suspension into an absorbent material, with or without subsequent drying.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (e.g. powder or granular) form for reconstitution with a suitable vehicle (e.g. sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or diglycerides. Other usual parentally-administrable formulations include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents; demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The pharmaceutical compositions of the invention may be dispensed to the subject under treatment with the help of an applicator. The applicator to be used may depend on the specific medical condition being treated, amount and physical status of the pharmaceutical composition, and choice of those skilled in the art.

The pharmaceutical compositions of the invention may be provided to the subject or the medical professional in charge of dispensing the composition to the subject, along with instructional material. The instructional material includes a publication, a recording, a diagram, or any other medium of expression, which may be used to communicate the usefulness of the composition and/or compound used in the practice of the invention in a kit. The instructional material of the kit may, for example, be affixed to a container that contains the compound and/or composition used in the practice of the invention or shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

Controlled Release Formulations and Drug Delivery Systems

In certain embodiments, the formulations of the present invention can be, but are not limited to, short-term release or rapid-offset release, as well as controlled release, for example, sustained release, delayed release and pulsatile release formulations.

The term short-term or rapid-offset release is used in its conventional sense to refer to a drug formulation that provides for release of the drug immediately after drug administration.

As used herein, short-term or rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments there between after drug administration after drug administration.

The term sustained release is used in its conventional sense to refer to a drug formulation that provides for gradual release of a drug over an extended period of time, and that may, although not necessarily, result in substantially constant blood levels of a drug over an extended time period. The period of time can be as long as a month or more and should be longer than the time required for the release of the same amount of agent administered in bolus form.

For sustained release, the compounds can be formulated with a suitable polymer or hydrophobic material that provides sustained release properties to the compounds. As such, the compounds of the invention can be administered in the form of microparticles for example, by injection or in the form of wafers or discs by implantation.

In a preferred embodiment of the invention, the compositions of the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

In a preferred embodiment of the invention, the compositions of the invention are administered to a subject, alone or in combination with another pharmaceutical agent, using a delayed release formulation.

The term pulsatile release is used herein in its conventional sense to refer to a drug formulation that provides release of the drug in such a way as to produce pulsed plasma profiles of the drug after drug administration.

In a preferred embodiment of the invention, the compositions of the invention are administered to a subject, alone or in combination with another pharmaceutical agent, using a pulsatile release formulation.

Dosing

The therapeutically effective amount or dose of a composition of the present invention will depend on the age, sex and weight of the patient, the current medical condition of the patient and the nature of the shivering or temperature spiking or pain or psychosis being treated. The skilled artisan will be able to determine appropriate dosages depending on these and other factors.

A suitable dose of a compound of the present invention may be in the range of from about 1 mg to about 5,000 mg per day, such as from about 10 mg to about 2,000 mg, for example. The dose may be administered in a single dosage or in multiple dosages, for example from 1 to 4 or more times per day. When multiple dosages are used, the amount of each dosage may be the same or different. For example a dose of 1 mg per day may be administered as two 0.5 mg doses, with about a 12 hour interval between doses.

In some embodiments, dose of a compound of the invention is between about 1 mg and about 3,000 mg. In some embodiments, a dose of a compound of the invention used in compositions described herein is between about 2 mg and about 1,000 mg. In some embodiments, a dose of a compound of the invention used in compositions described herein is between about 4 mg and about 500 mg. In some embodiments, a dose of a compound of the invention used in compositions described herein is between about 8 mg and about 250 mg. In some embodiments, a dose of a compound of the invention used in compositions described herein is between about 16 mg and about 125 mg. In some embodiments, a dose of a compound of the invention used in compositions described herein is between about 30 mg and about 60 mg, and any and all whole or partial increments there between.

It is understood that the amount of compound dosed per day may be administered every day, every other day, every 2 days, every 3 days, every 4 days, every 5 days, etc. For example, with every other day administration, a 5 mg per day dose may be initiated on Monday with a first subsequent 5 mg per day dose administered on Wednesday, a second subsequent 5 mg per day dose administered on Friday, etc.

The compounds for use in the method of the invention may be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Experimental Details

Materials

Peptide synthesis reagents were purchased from Perseptive Biosystems (Foster City, Calif.). Hemin was purchased from Fluka (St. Louis, Mo.). The chloride salt of $Fe^{3+}$-protoporphyrin III was synthesized by methods described previously [51]. Deuterium oxide, $^{15}N$-ammonium chloride, $^{13}C$-glucose and (trimethylsilyl)propionate were obtained from Cambridge Isotope Laboratories (Andover, Mass.). All other solvents and reagents were obtained from Fisher Scientific (Pittsburgh, Pa.) or Sigma (St. Louis, Mo.).

Preparation and Purification of Constructs 1-5.

Construct 1 corresponds to SEQ ID NO:5. Construct 2 corresponds to the cystine derivative of SEQ ID NO:6. Construct 3 corresponds to the cystine derivative of SEQ ID NO:7. Construct 4 corresponds to the cystine derivative of SEQ ID NO:8. Construct 5 corresponds to the cystine derivative of SEQ ID NO:9.

Protein expression, purification and confirmation of purity were performed as described previously [22].

Solid-phase syntheses of Constructs 1-5 were performed on a continuous flow PerSeptive Biosystems (Foster City, Calif.). Crude peptides were purified to homogeneity by reverse phase $C_{18}$ HPLC using aqueous-acetonitrile gradients containing 0.1% (vol/vol) trifluoroacetic acid. Peptide homogeneity and composition were assayed by analytical HPLC and laser desorption mass spectrometry.

Preparation and Purification of Constructs 6-11.

Construct 6 corresponds to the amino acid sequence of cystine derivative of SEQ ID NO:1. Construct 7 corresponds to the amino acid sequence of SEQ ID NO:11. Construct 8 corresponds to the amino acid sequence of SEQ ID NO:12. Construct 9 corresponds to the amino acid sequence of SEQ ID NO:13. Construct 10 corresponds to the amino acid sequence of SEQ ID NO:14. Construct 11 corresponds to the amino acid sequence of SEQ ID NO:15. Construct 12 (AP6) corresponds to the amino acid sequence of SEQ ID NO:17. Construct 13 (AP6a) corresponds to the amino acid sequence of SEQ ID NO:18. Construct 14 (AP6b) corresponds to the amino acid sequence of SEQ ID NO:19. Construct 15 (AP6c) corresponds to the amino acid sequence of SEQ ID NO:20.

The preparation and purification of Constructs 6-11 is exemplified in a non-limiting manner below. The gene encoding Construct 6 was designed using the program Amplify [52]. The gene was constructed using assembly PCR [53] and ligated into the overexpression vector pET32d(+) (Novagen, Inc., Gibbstown, N.J.) modified to replace the enterokinase cleavage site with a TEV-protease cleavage site, yielding the plasmid pHP7-TEV. The plasmid was transformed into DH5-alpha cells and sequenced in the region of interest to verify the presence of the intact gene, and the plasmid was transformed into BL21(DE3) cells. Mutations to Construct 6 were created using the Quick Change protocol (Stratagene, Inc., Santa Clara, Calif.).

For unlabelled expression, these cells were grown in TPP medium [54] at 37° C. to a $D_{600}$ of 1.0 and induced with IPTG at a final concentration of 1 mM for 2 h before collection. For $^{15}N$-labelled expression, cells were grown at 37° C. in minimal media containing 1 g/liter $^{15}N$ ammonium chloride to a $D_{600}$ of ~1.0, induced with 1 mM IPTG, and shaken at 37° C. for an additional 3 h. For $^{13}C$ $^{15}N$-double labeling, cells were grown in minimal media containing 1% w/v $^{13}C$-glucose, 1 g/liter $^{15}N$-ammonium chloride and 8 ml/liter $^{13}C,^{15}N$-Bioexpress medium (Cambridge Isotope Labs, Andover, Mass.). Cells were grown at 37° C. to a $D_{600}$ of ~1.0, induced with 1 mM IPTG, and shaken at 37° C. for an additional 2 h.

Cells were collected by centrifugation, broken open using a French press, and purified on a Ni-nitrilotriacetic acid column (Qiagen, Inc., Hilden, Germany), according to the manufacturer's instructions. The fusion protein was dialysed into 50 mM Tris-HCl, 1 mM DTT, pH 8.0, and then cleaved overnight (15-18 h) with $His_6$-tagged TEV protease (Invitrogen, Inc., Carlsbad, Calif.). The reaction mixture was filtered through Ni-nitrilotriacetic acid resin, and the purified Construct 6 was concentrated by lyophilization. Purified peptides were dissolved in 20 mM $K_2HPO_4$ and 100 mM KCl, pH 8.0, and cysteine residues were air-oxidized to the symmetric disulfides (cystine residues) overnight. Disulfide formation was followed by analytical $C_{18}$ HPLC.

Preparation and Purification of Constructs 12-15.

Constructs 12-15 were synthesized on a continuous-flow solid-phase synthesizer (either Pioneer from Applied Biosystems or Liberty Microwave Peptide Synthesizer from CEM, Matthews, N.C.) on a Fmoc-PEG-PAL-PS resin (Applied Biosystems) at 0.1 mmol scale. The peptides were cleaved from the resin and simultaneously deprotected using 90:8:2 trifluoroacetic acid-ethanedithiol-water for 2 h.

Crude peptides were precipitated with cold ether and purified to homogeneity by reversed-phase $C_{18}$ HPLC using aqueous acetonitrile gradients containing 0.1% (v/v) TFA. The purity and molecular weight of the acetylated peptides were confirmed by matrix-assisted laser desorption/ionization mass spectrometry (MALDI-MS).

FTIR.

In a representative but non-limiting procedure, Construct 6 was washed by dilution with 100 mM potassium phosphate and 100 mM KCl at pH 6.0 or pH 8.0 and concentrated to ~1 mM with Vivascience (Littleton, Mass.) centrifugal concentrators. Benzyl viologen (100 microM) was added as a redox mediator and the sample was placed in a micro-electrochemical chamber above an ATR-FTIR microprism (3 bounce silicon; 3 mm diameter) by SensIR (Watford, Herts, UK). The chamber had a 5-mm-diameter glassy carbon working electrode within 1 mm of the prism surface and the sample solution was connected to a counter electrode and an Ag/AgCl reference electrode via an ion-permeable frit. Potential was switched cyclically between 0 mV and −450 mV (versus SHE). Before each potential change, a reference scan was recorded. The potential was then switched and a sample spectrum was recorded after 10 min to allow for redox equilibration. Data at pH 6.0 average 50 reductive minus 50 oxidative cycles of 500 interferograms each at 4 $cm^{-1}$ resolution; data at pH 8 average 40 reduced minus oxidized cycles; the double difference spectrum pH 6 minus 0.58 pH 8 reflected appropriate protein concentration-dependent weighting at the two pH values.

Kinetics for Binding of Gases to Construct 6.

Predominantly mono-exponential binding kinetics of $O_2$ and CO with the ferrous heme B in Construct 6 were followed spectroscopically in rapid stopped-flow mixing over gas concentrations from 2% to 50% saturation at 15° C. using an Olis RSM 1000 spectrometer (Bogart, Ga.) that scans both the alpha band and Soret band absorptions 1,000 times a second, followed by SVD analysis of the kinetic components. The dissociation rate of the CO complex was determined by competition with ferricyanide using a range of ferricyanide concentrations according to the ferric heme trapping method described previously [44].

Preparations of ferrous heme synthetic proteins in CO saturated 30% ethylene glycol borate buffer at pH 9.0 were stable to ligand exchange on a timescale of several minutes in the dark at −15° C. This allowed spectra such as those shown in FIG. 2 to be prepared by re-equilibration with $O_2$ or $O_2$/CO gas mixtures, followed by photolysis by halogen lamp illumination for several seconds to initiate rapid $O_2$ binding, as described previously [26].

Example 1

Assembly of Scaffold and Cofactors

Construct 1 comprised polar glutamate (E) and lysine (K), as well as non-polar leucine (L) (FIG. 1). These amino acids have high α-helix-forming propensities [1,3], which, when arranged in a near-repeating heptad sequence LEELLKKLEELLKL (SEQ ID NO:10), spontaneously assemble into a water-soluble four-α-helical bundle with glutamate and lysine exposed and leucine buried in a molten globular interior [1,4]. To make a bundle of a length typical of natural proteins, almost four heptad near-repeats were used, affording Construct 1 (FIG. 1).

Example 2

Insertion of Cofactor-Binding Amino Acids

A bundle such as Construct 1 is free to associate with helices oriented parallel or anti-parallel. Adding an amino-terminus CGGG sequence for disulfide-mediated dimerization should restrict helical topologies to syn or anti. Completing this stage, an internal leucine at e-position 7 of each helix was replaced with tryptophan to facilitate optical detection of the protein. As a next step in the design, replacement of the leucines at internal a-positions 10 and 24 with histidine was sufficient to anchor up to four hemes in the bundle [1,5]. The a-position leucine 17 between the hemes was replaced with phenylalanine, an amino acid commonly found near hemes in natural proteins. To allow distinguishing between the heme-binding sites, another interior leucine was replaced with arginine, resulting in Construct 2 (FIG. 1). No effort was made to design core cavities that accommodate heme. Rather, reliance was put on interior histidine-iron ligation to position the heme in a malleable hydrophobic interior.

Example 3

Improvement of Structural Resolution

Packing the Apo Core

Structural resolution may be helpful in keeping progressive design on track. Singular structures in these bundles may be engineered without computation; introduction of β-branched aliphatic or aromatic residues along with a polar bond across helices provided by the histidines (Construct 3 in FIG. 1) conferred tertiary structure to the four α-helix interior of the apoprotein as seen by NMR and X-ray crystallography [16, 17].

Example 4

Improvement of Structural Resolution

Removing Excess Heme Sites and Improving Hobo Helical Register.

Although various functions may be added to this basic heme-binding protein, for the sake of oxygen transport the design was simplified by lowering the heme capacity from four to two by replacing histidine at position 24 with phenylalanine. Inspection of model apo structures showed that a substantial rotation of >50° around the helical axes upon heme binding was required to accommodate the histidine rotamers typical of natural bis-histidine heme-binding proteins [18]. This rotation exports hydrophobic interior residues into, and imports polar residues from, the aqueous phase. Modeling identified four amino acids for substitution to interfacially compatible alanines or glutamines [1,9] and one for deletion to realign the binary pattern more favorably after heme addition, yielding Construct 4 (FIG. 1). However, three inwardly rotating b-position glutamates at positions 11, 18 and 25 were deliberately left in place [1,8] to apply strain to weaken one of the two histidine-heme iron ligation interactions, as occurs in neuroglobin. This creates an entatic state [20]. Fourier transform infrared spectroscopy (FTIR) showed that these strain-inducing glutamates have pK values (that is, pH values at which the residues are half protonated) increased by more than two units and, as in natural heme proteins, were strongly electrostatically coupled to heme oxidation-reduction, changing the pK by more than three units [21]. NMR showed that addition of two heme Bs transformed unstructured apo-Construct 4 into a well-defined tertiary structure [22]. The histidine-iron polar bond may also provide a nucleus for interior packing that promotes a singular structure around different porphyrin cofactors [22]. To ease NMR structure determination and assignment of 90% of the peptide backbone, external residues were also diversified at this time, yielding Construct 5 (FIG. 1).

Example 5

Exclusion of Water for Oxy-Ferrous Heme Stability

Constructs 1-5 did not bind $O_2$ stably at room temperature. In fact, none of the artificial hemes proteins examined above were able to bind this gas stably at room temperature [23, 24, 25]. This result does not indicate that the oxy-ferrous heme cannot be formed. Constructs 2, 3, 4 and 5 all include the glutamate-based helical strain, which weakens the histidine ligation and allows competition from other ligands. By first exposing these heme proteins to CO and then illuminating at a low temperature to initiate ligand exchange for $O_2$, as was done previously with cytochrome oxidase [26], each formed an oxy-ferrous heme at near 100% yield at −15° C. The probable reason for room temperature instability was the access of water and protons to the heme-binding site, which facilitates electron transfer from ferrous heme to oxygen. This is clear from mutant studies of globins and the relative stability of the oxy-ferrous heme in chemical systems in water-free solvents [11,27,28].

Example 6

Spectral Analysis of Constructs

To engineer water exclusion, the potentially culpable protein motion was constrained. The crystal and NMR structures of Construct 3 revealed that one of the two interhelical interfaces (specifically the one that lies between the helices not constrained by heme binding) had an unusually low degree of surface complementarity and a high degree of inter-helix motion. Indeed, Construct 2 could be modified to introduce large-scale syn-anti flipping [29]. To constrain motion, the loops were reconfigured to link the helices across the most mobile interface. This also allowed the loops to be linked into a monomeric "candelabra" structure, further constraining motion (Construct 6 in FIG. 1). NMR confirmed the waterrestricting effects of loop reconfiguration and monomerization. Hydrogen isotope (H/D) analysis of hydrogen exchange protection factors of Constructs 4 and 6 at pH 7 and 25° C. (data not shown) showed that water-mediated proton exchange was complete within 15 min for Construct 4 and was much slower for Construct 6 with several core residue backbone amides, including some close to the heme, exchanging on a timescale of several hours.

A stopped-flow spectroscopy experiment of Construct 6 with CO showed rapid displacement of one histidine to generate an indefinitely stable carboxy-ferrous heme species in a 400-ms half time (not shown). After CO photolysis, CO rebinding to Construct 6 was multiphasic (FIG. 3), as observed in the hexacoordinate globins. Detailed analysis of these data allowed the estimation of the histidine on- and off-rates, as summarized in Table 1.

TABLE 1

Heme iron ligand on-and off-rates and equilibrium constants in natural and artificial proteins.

| Haem protein | Ligation | $k_{His\,on}$ ($s^{-1}$) | $k_{His\,off}$ ($s^{-1}$) | $k_{CO\,on}$ ($\mu M^{-1}s^{-1}$) | $k_{CO\,off}$ ($s^{-1}$) | $K_{dCO}$ (nM) | $k_{O2\,on}$ ($\mu M^{-1}s^{-1}$) | $k_{O2\,off}$ ($s^{-1}$) | $K_{dO2}$ (nM) | $K_{dO2}/K_{dCO}$ |
|---|---|---|---|---|---|---|---|---|---|---|
| 6 (haem B) | bis-His | 310 | 17 | 0.95 (0.006) | 0.034 | 36 (6,000) | 0.31 (0.017) | 0.1 | 32 (600) | (0.1) |
| Neuroglobin[31] | bis-His | 2,000 | 4.5 | 65 (0.15) | 0.014 | 0.21 (93) | 250 (0.56) | 0.8 | 3.2 (1,400) | (15) |
| Myoglobin[47] | His-aquo (distal His) | n/a | n/a | 0.5 | 0.019 | 37 | 14 | 12 | 860 | 23 |
| Human haemoglobin[48] | His-aquo (distal His) | n/a | n/a | 2.2 | 0.009 | 4 | 19 | 15 | 770 | 190 |
| *Ascaris* haemoglobin[49] | His-aquo (distal Tyr) | n/a | n/a | 0.2 | 0.018 | 90 | 1.5 | 0.004 | 3 | 0.03 |
| Micro-peroxidase[50] | His-aquo | n/a | n/a | 20 | 0.01 | 0.5 | | | | |
| Combinatorial bundles[44] | Mixed | ? | ? | (3-11) | 0.03-0.11 | (6-25) | | | | |

Apparent binding rates (in parentheses) are slowed by bis-histidine (bis-His) ligation. Corresponding rates not in parentheses are estimated binding rates without histidine impedance facilitating comparison with proteins with different fractions of bis-histidine ligation. His-aquo has water as the sixth iron ligand.
n/a, not applicable;
?, unknown.

Constructs 2-6 displayed ferric and ferrous heme visible spectra that were indicative of six-coordinate bis-histidine ligated heme B—characteristic of cytochrome b, deoxy-neuroglobin and cytoglobin, and quite distinct from the five-coordinate myoglobin and hemoglobin. Because the dissociation constant ($K_d$) for binding of the first heme (<1 nM) was much tighter than that for the second heme (50 nM) [22], spectral analysis was simplified by binding one heme per bundle (FIG. 2A). NMR assignments unambiguously identified the first heme B to bind at H7 positions at the open end of the candelabra structure of Construct 6. Only ferrous heme Construct 6 showed rapid and complete conversion of the ferrous heme into the oxy-ferrous heme with a half time of ~50 ms measured by stopped-flow spectroscopy. This oxy-ferrous spectrum was remarkably similar to that of native neuroglobin. The oxy-ferrous state was stable for tens of seconds before single electron transfer from ferrous heme to $O_2$ appears to generate superoxide.

Example 7

Binding of CO to Constructs

Figure 3A:
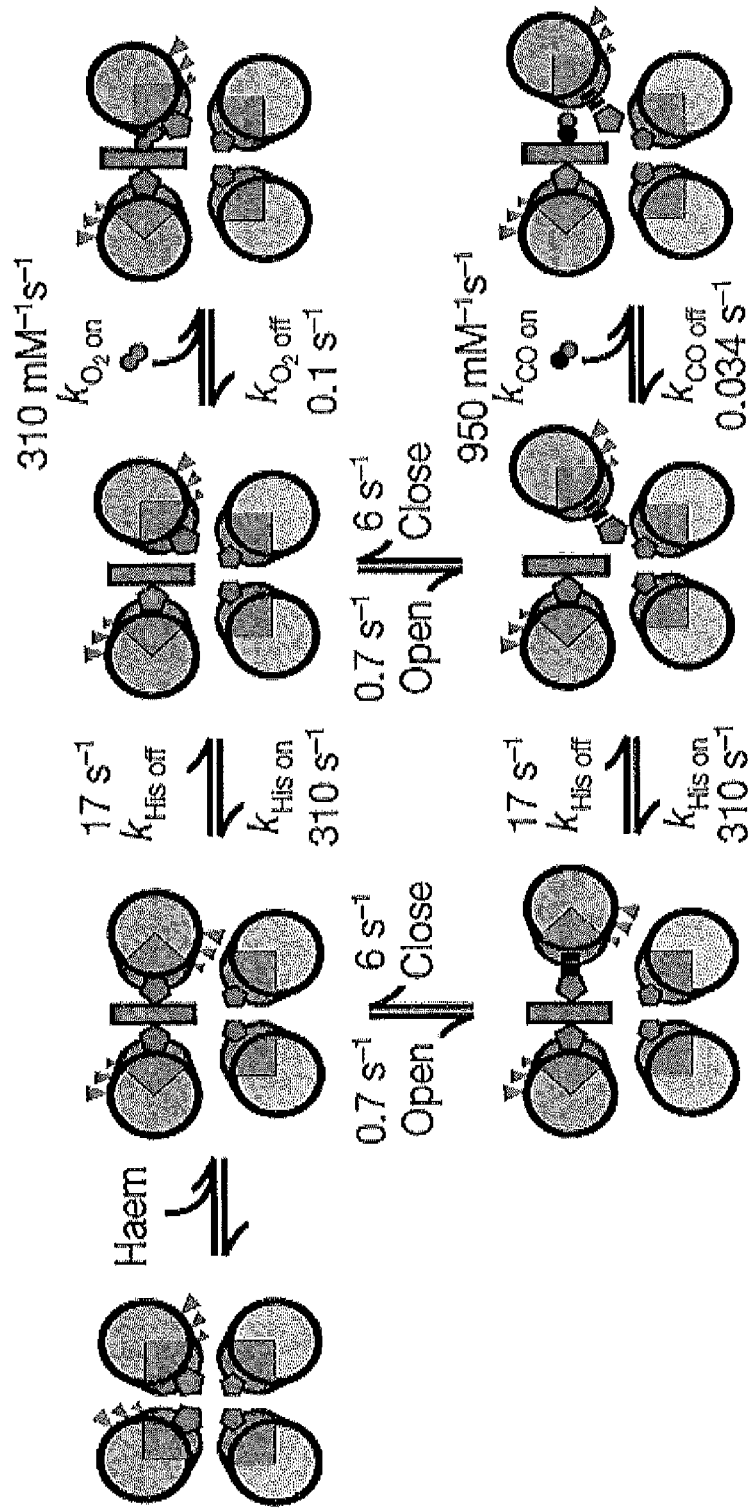
FIGS. 3A-3D, illustrates the modeling kinetics of heme ligand binding and release.
Figure 3B:
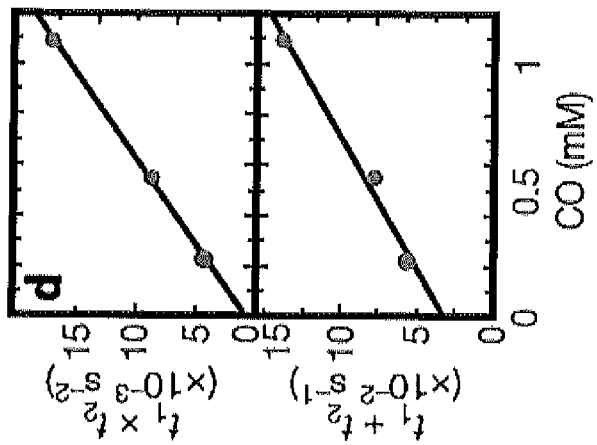
Figure 3C:
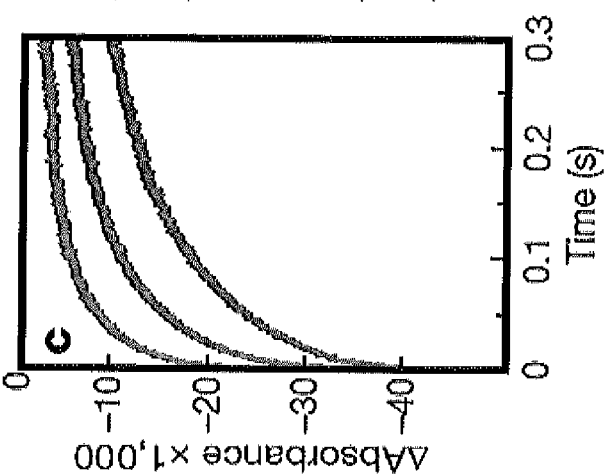
Figure 3D:
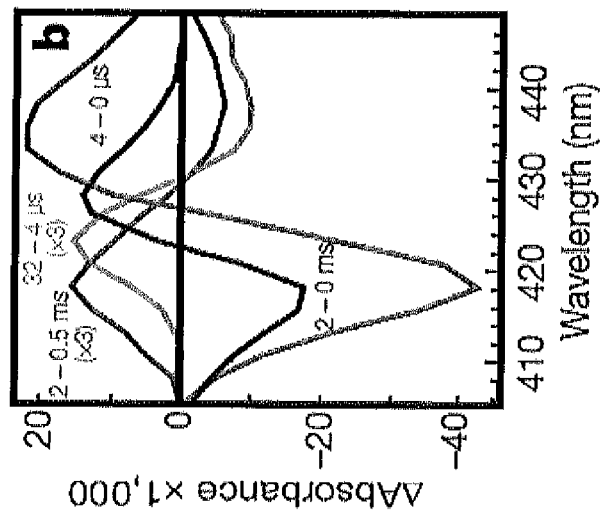

CO rebinding after photolysis by a frequency-doubled YAG laser at 532 nm, with a ~1-ns pulse width (FIG. 3C), was multi-exponential, a characteristic signature of human neuroglobins [45]. Detailed analysis of time-resolved spectra in the flash experiments was consistent with a rapid exponential phase due to a change in pentacoordinate heme conformation (FIG. 3B), similar to that reported for myoglobin [46]. After this relaxation, slower biphasic kinetics were associated with direct CO and histidine binding, followed by final histidine-CO exchange. Using the kinetic model of Hargrove [45] to analyze the CO-concentration-dependence of the CO binding rates on flash photolysis allowed the estimation of histidine on- and off-rates and percent bis-histidine ligation for ferrous Construct 6 (FIG. 3D).

CO rapid mixing showed slower binding than expected from photolysis, indicating the presence of at least two conformations that differ in CO accessibility, termed "open" and "closed" in analysis of hexacoordinate hemoglobins [30]. Saturation of the observed CO binding rate allowed estimates of the opening and closing rates. Competition between CO recombination and oxidation by added ferricyanide also allowed an estimation of the rate of thermal CO dissociation. Table 1 presents the kinetic constants (also shown in FIG. 3A) and equilibrium binding constants that have been determined for Construct 6 and contrasts them with several natural oxygen-binding proteins. Whereas the oxygen off-rate was similar to that of human neuroglobin [31], the on-rate is almost 100 times slower and resembles that of *Ascaris* hemoglobin. These artificial proteins are robust and adaptable enough to redesign for the testing of the hypothesis that a large hydrophobic pocket, as in neuroglobin [32], can speed $O_2$ binding, whereas proximal strain, as in *Ascaris* hemoglobin [33], slows $O_2$ binding.

Example 8

Testing Engineering Elements

To test whether the helical rotation model of histidine strain was indeed operating to promote CO and $O_2$ binding, the b-position glutamates of Construct 6 was changed to alanines. As anticipated, CO binding slowed by more than an order of magnitude. Moreover, $O_2$ failed to form detectable oxy-ferrous heme. Instead, the heme underwent oxidation within the mixing time, plausibly by means of an outer sphere electron transfer. Thus, removal of the modeled entatic state [20] by conversion of interfacial glutamates to alanines disables the histidine for $O_2$ or CO exchange-gated rotational mechanism.

In exploring the effectiveness of loops to control mobility of free helices and thereby exclude water from the interior, the oxy-ferrous heme was found not to be stabilized by looping together helices already linked by heme (Construct 5), but to be stabilized by looping together helices not linked by heme (Construct 6). Disulfide linkage of the loops in Construct 6 proved unessential, because eliminating the disulfide through a Cys-to-Ser substitution maintained oxy-ferrous heme stability.

The development of helical strain and motion constraint to promote $O_2$ binding to ferrous heme was not confined to one site, but extended along the four-helix bundle to hemes at other positions. Both a di-heme variant of Construct 6 with histidine at position 7 and the complementary position 42, and a single-heme variant with histidine only at position 42, displayed oxy-ferrous heme properties similar to that observed in Construct 6.

Example 9

Heme and Substrate Specificity

The interior of Construct 6 adopted a unique structure not only around heme B but also around other porphyrins including heme A. Heme A had markedly different peripheral substitutions (FIG. 2B), resulting in different redox and spectral properties. The oxidation-reduction midpoint potential at pH 8 ($E_{m8}$) measured versus the normal hydrogen electrode (NHE) of bound heme A was −100 mV. This is about 200 mV more positive than heme B and hence less favored to reduce $O_2$ to $O_2^{\cdot-}$. Accordingly, the oxy-ferrous heme A, spectrally analogous to the cytochrome oxidase Compound A described previously [26], persisted longer, about half a minute, before electron transfer.

In all natural hemoglobins with distal histidines, either preferentially bound to the heme iron, as in neuroglobin, or displaced from the iron, as in myoglobin or human hemoglobin, CO is a poison that binds more tightly than $O_2$. The present results show that this is not an essential property. The binding of CO to Construct 6 was weaker than to natural globins (Table 1). This resulted in a net tenfold discrimination favoring $O_2$ binding over CO binding, the largest observed for any distal histidine heme-protein complex, and comparable to distal tyrosine sites with extreme $O_2$ affinity. It seems probable that the strained, distal histidine in Construct 6 remains available to stabilize bound oxygen, as is seen in hemoglobins, myoglobins and horseradish peroxidase [34].

Example 10

Protein Malleability

Figure 4:
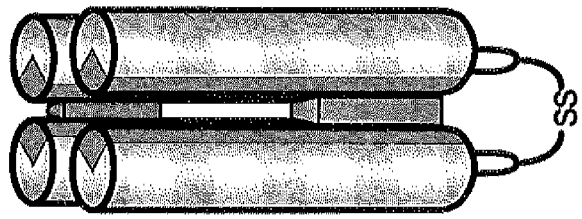
FIG. 4 is a graphical illustration of the four-helix bundle structure of Construct 6, which corresponds to the cystine derivative of SEQ ID NO:1.
Figure 5:
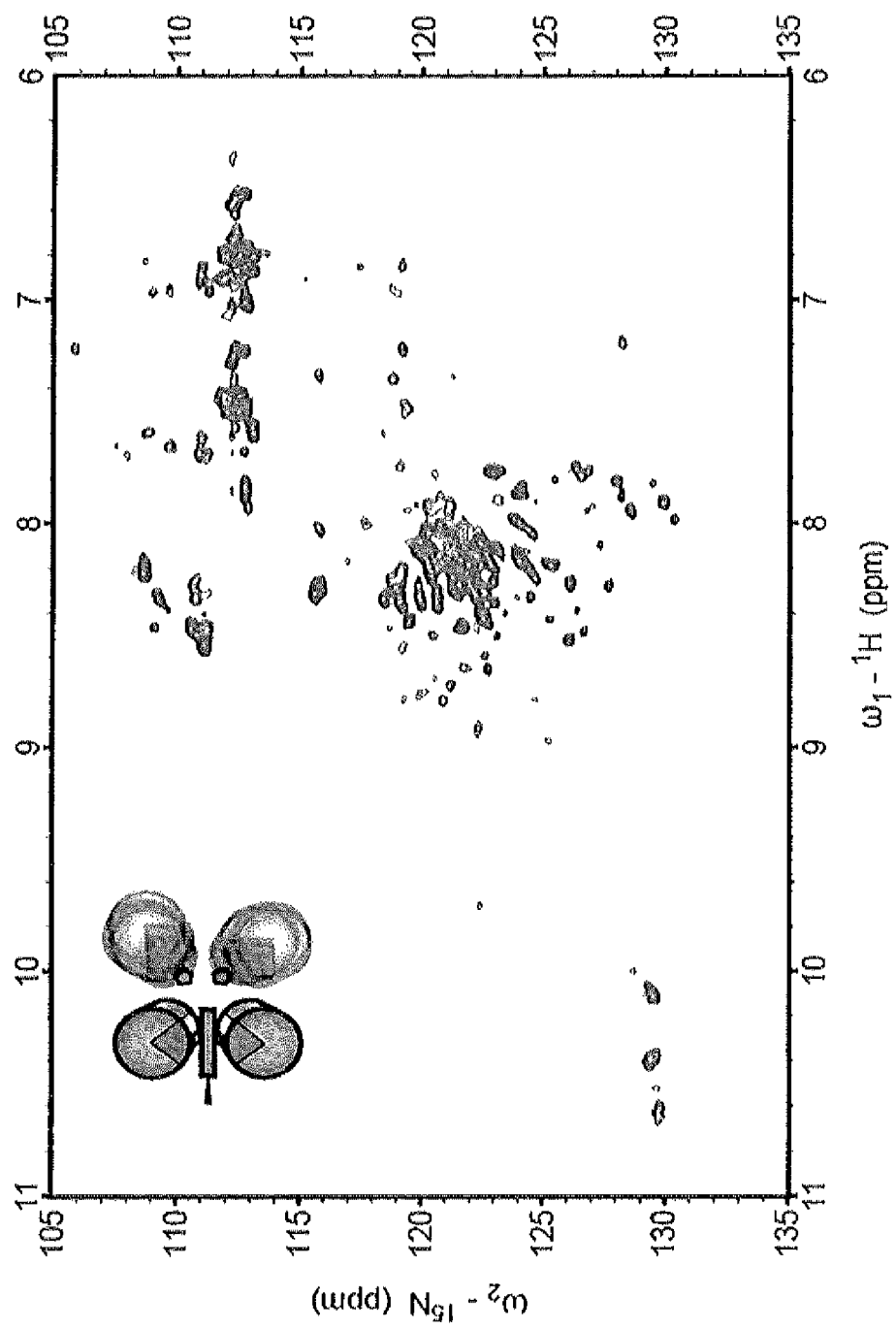
FIG. 5 illustrates a HSQC NMR spectrum of Construct 6 complexed with Heme A.

Protein malleability in Construct 6 (FIG. 4) was evaluated by complexing Construct 6 with heme A, which differs in structure from heme B. The replacement of heme B with heme A caused considerable protein restructuring, as evidenced by an HSQC NMR spectrum (FIG. 5). This result suggests that the prototype protein is a versatile platform for a variety of heme structures.

Example 11

$O_2$ Binding Characteristics

Figure 6A:
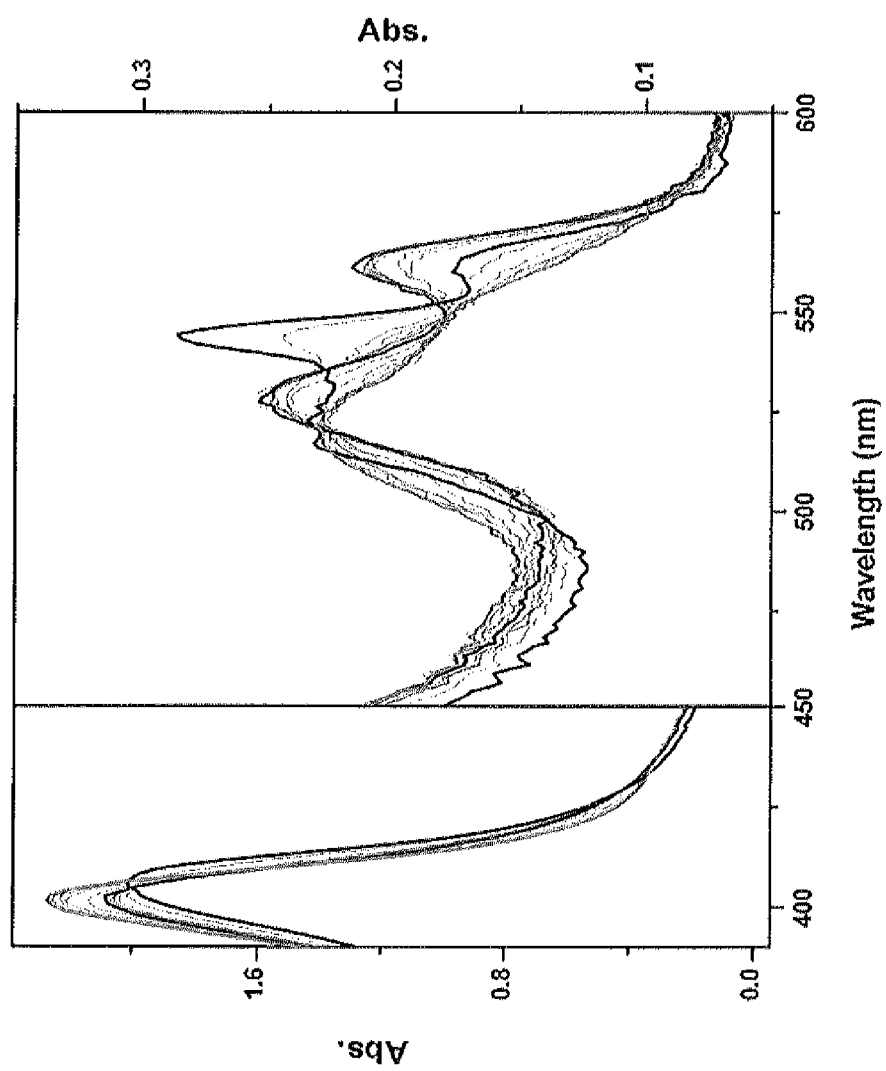
FIGS. 6A-6C, is a series of graphs depicting the kinetics of $O_2$ binding to Construct 6 complexed with mesoheme (FIG. 6A) and deuteroheme (FIG. 6B).
Figure 6B:
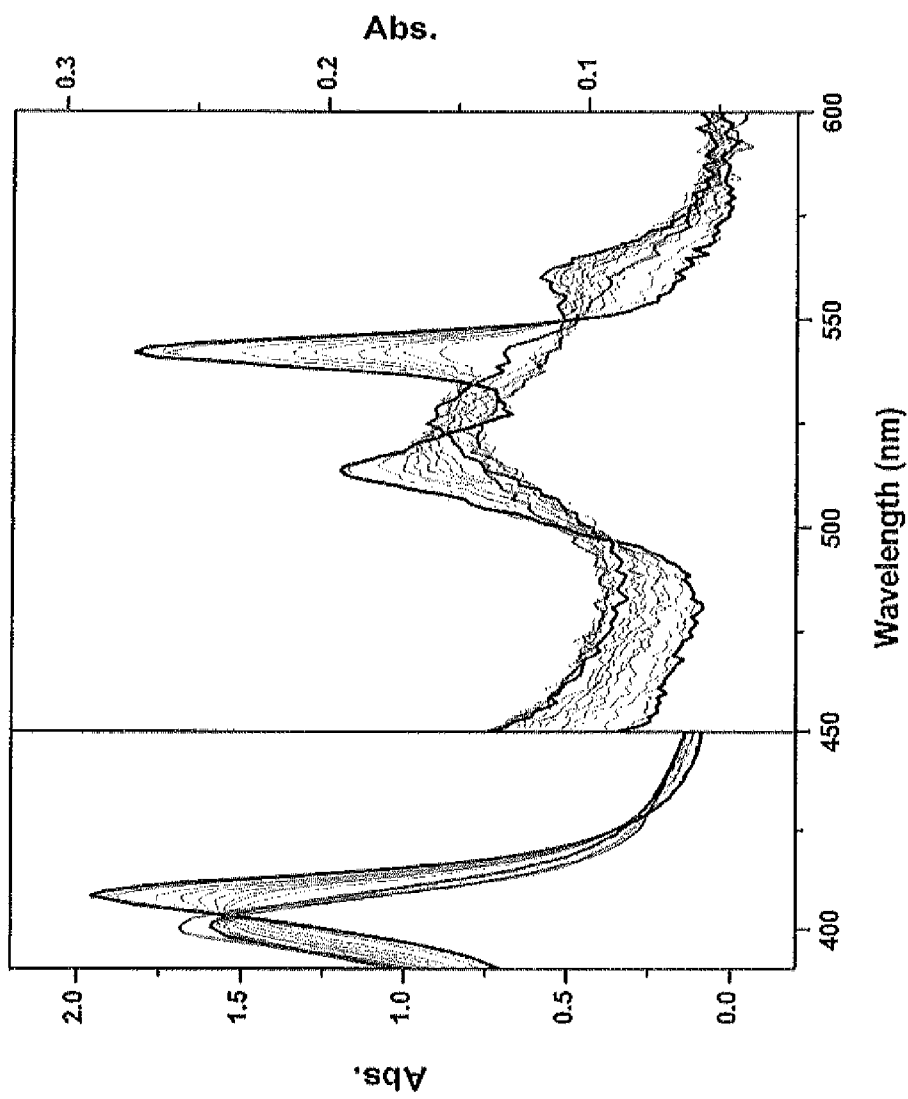
Figure 6C:
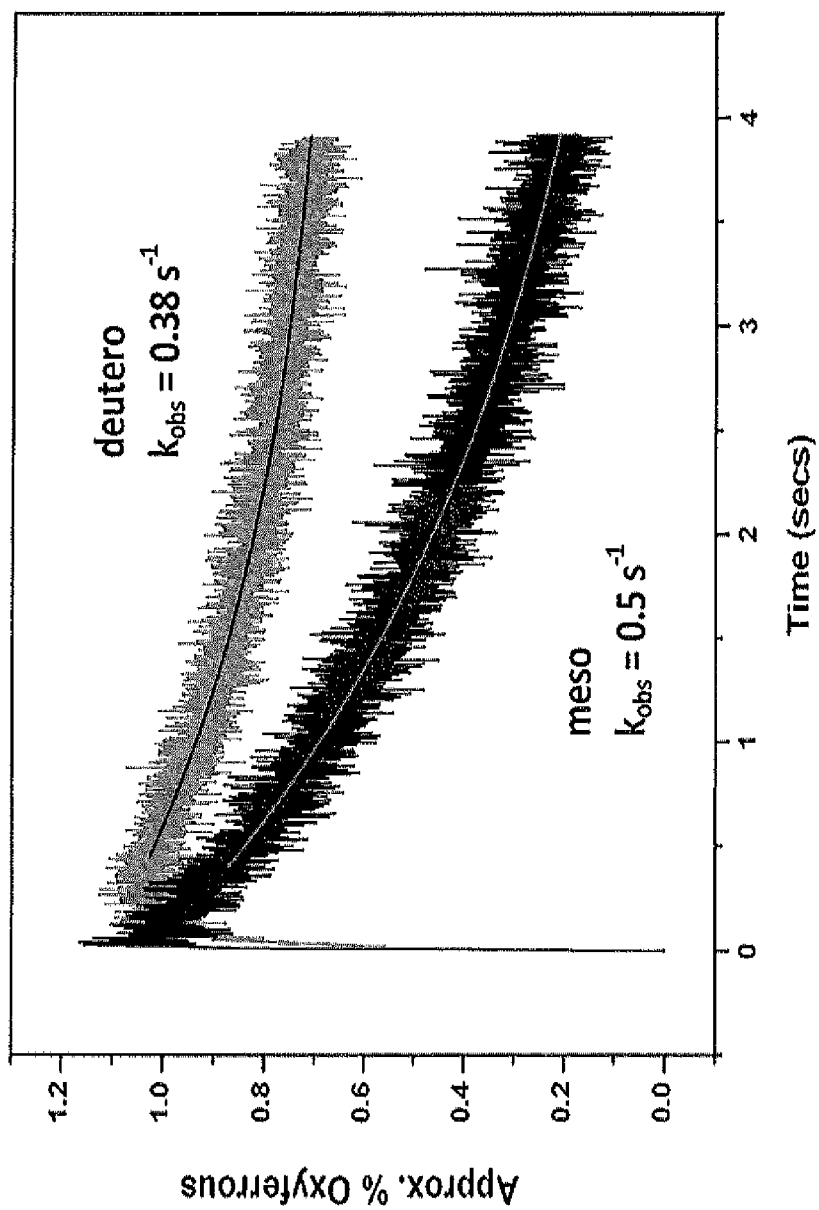

Construct 6 complexed with mesoheme and deuteroheme was still capable of binding $O_2$, but with different kinetics (FIG. 6).

Analysis of the UV-vis spectra as a function of time allowed the calculation of the following kinetic constants for decay of the oxyferrous state:

(a) Construct 6/deuteroheme: $k_{obs}$=30 sec$^{-1}$
(b) Construct 6/heme B: $k_{obs}$=30 sec$^{-1}$
(c) Construct 6/meso B: $k_{obs}$>100 sec$^{-1}$ For comparison, the observed kinetic constant for $O_2$ binding to the construct of amino acid sequence (SEQ ID NO:2)-(SEQ ID NO:25)-(SEQ ID NO:2)/heme B was $k_{obs}$=0.35 sec$^{-11}$.

Example 12

Design of Single Chain Four-Helix Bundles

Single chain four-helix bundle peptides were designed based on helix-turn-helix cystine derivatives described above. The amino acid sequences of Constructs 7-9 are illustrated in FIG. 7. The amino acid sequences of Constructs 7-11, along with the helix number assignments, are illustrated in FIG. 8.

Figure 9:
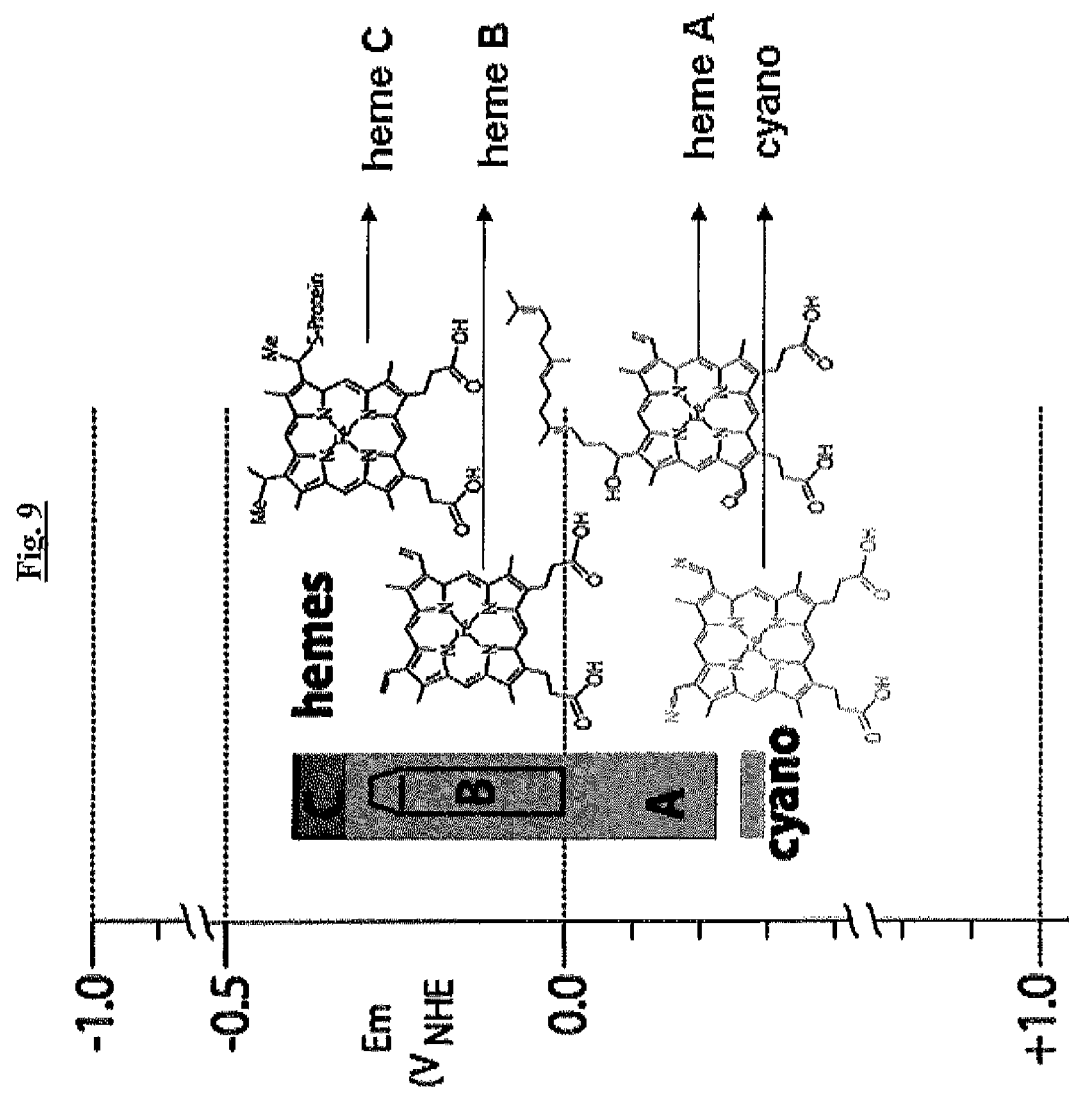
FIG. 9 illustrates the structures and ranges of potentials for different hemes bound to Constructs 6 and 7.

Constructs 7-11 were expressed in *E. coli* BL21(DE3)-RIL as a C-terminus fusion to GST. Purification on a nickel column, followed by cleavage from the fusion via a TEV cut site afforded constructs with an additional N-terminal glycine residue (except for Construct 11). FIG. 9 illustrates the structures and ranges of potentials observed for different hemes bound to Constructs 6 and 7.

In one aspect, the single chain four-helix bundle peptides differ from the corresponding cystine derivatives, because the symmetry restrictions in the protein design were removed in the single chain constructs.

In another aspect, the single chain four-helix bundle peptides described herein may be processed using intein technology, whereby expressed proteins are combined with synthesized peptides.

Example 13

Characterization of Construct 7

Figure 10:
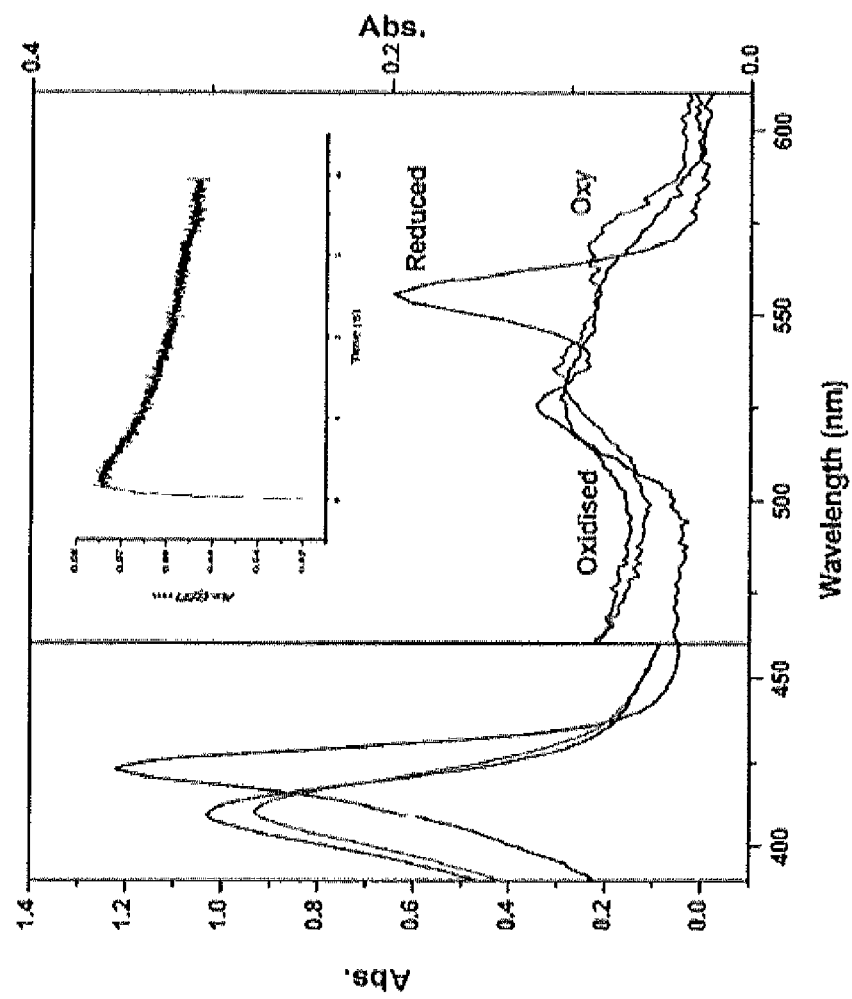
FIG. 10 illustrates the formation of oxy-ferrous state in hemin bound Construct 7 in a stopped flow experiment. Spectra panels show Soret (left) and alpha-beta bands (right) of intermediates determined by SVD analysis of the full spectra kinetics traces. Oxidized, reduced and oxy-ferrous states are distinctly visible.

FIG. 10 suggests that Construct 7 retained the $O_2$ binding functionality of Construct 6. The spectral data further suggest that the covalent heme C retained the functional characteristics seen in Construct 6 and Construct 7 with other hemes. The results also suggest that Construct 7 still incorporates the built-in strain on the heme iron ligation that permits $O_2$ binding. This result further suggests that in Construct 10 water access to the heme is still restricted, preventing destabilization of the ferrous heme $O_2$ state, which is critical for the function of $O_2$ transport.

Example 14

In Vivo c-Type Maturation

Figure 11:
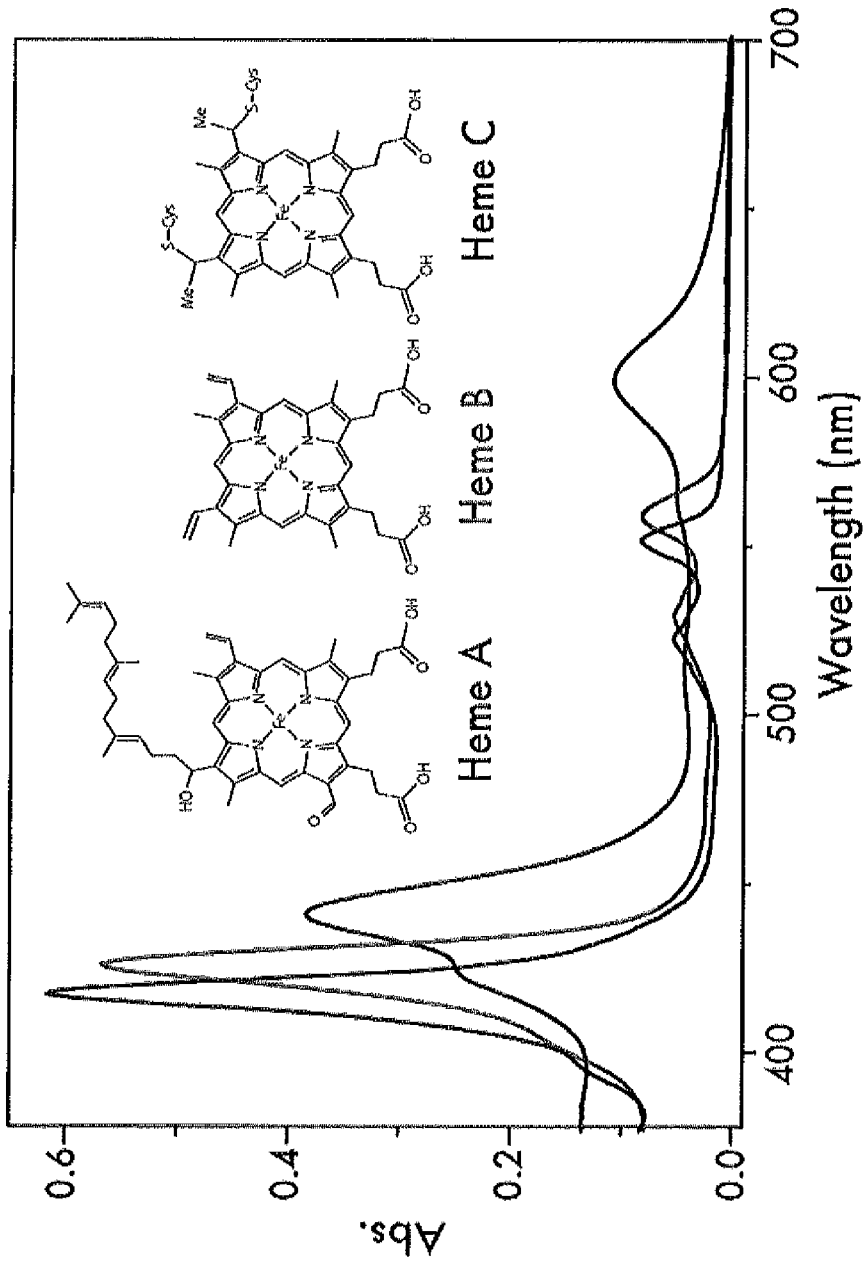
FIG. 11 illustrates the overlay of UV-spectra for ferric state of Construct 7 bound to Heme A and Heme B, as well as Construct 10 covalently bound to Heme C.

Expressing Construct 10 with a periplasmic export tag in *E. coli* BL21(DE3) constitutively expressing a c-type maturation operon on the pEC86 vector generated a majority of the dithioether modified c-type, as illustrated in FIG. 11. This experiment demonstrated the in vivo incorporation of a cofactor at a single site in Construct 10.

Figure 12:
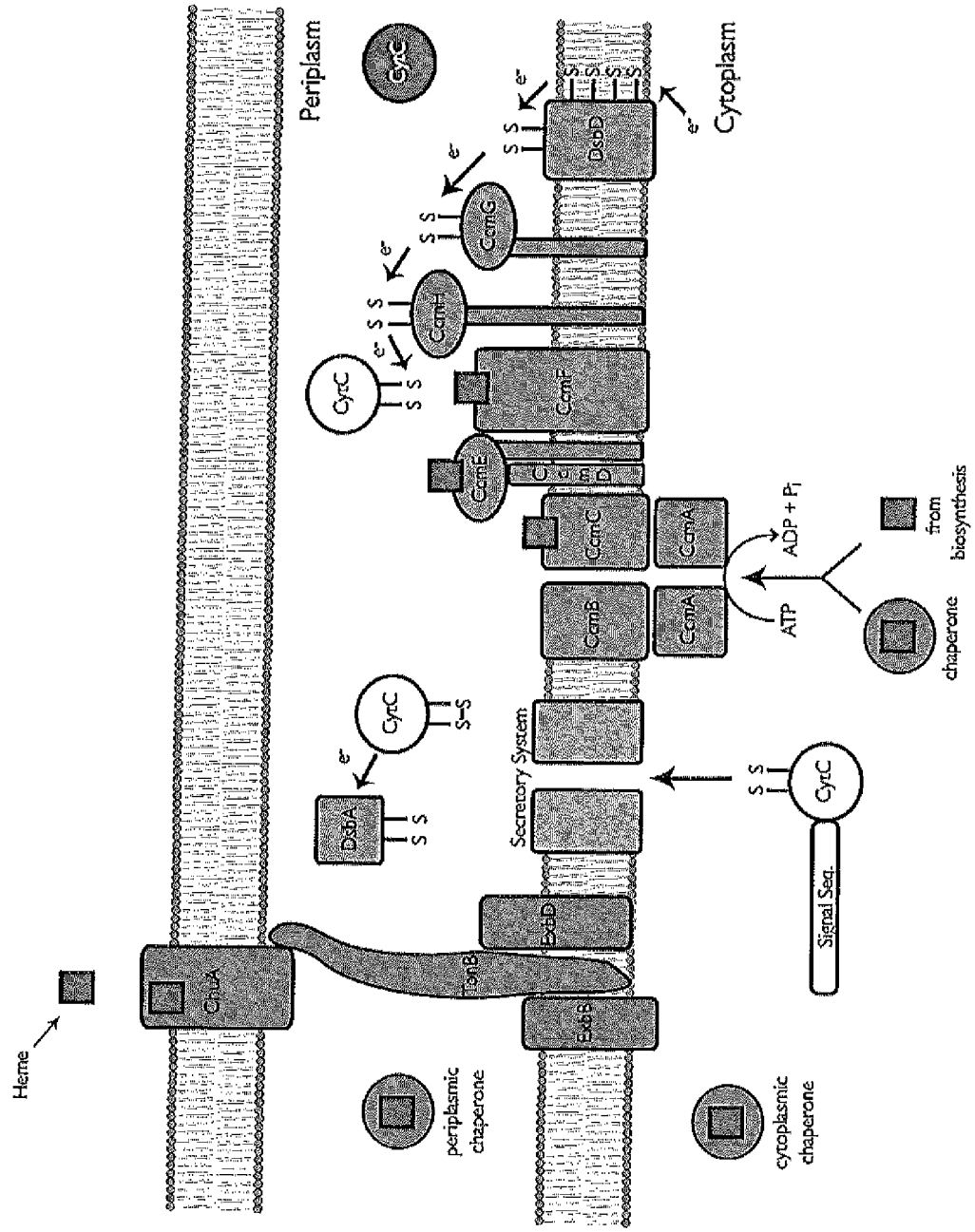
FIG. 12 illustrates the maturation system for Construct 10 designed for expression in the periplasm.

The Construct 10 maturation system designed for expression in the periplasm or cytoplasm is illustrated in FIG. 12.

Figure 13:
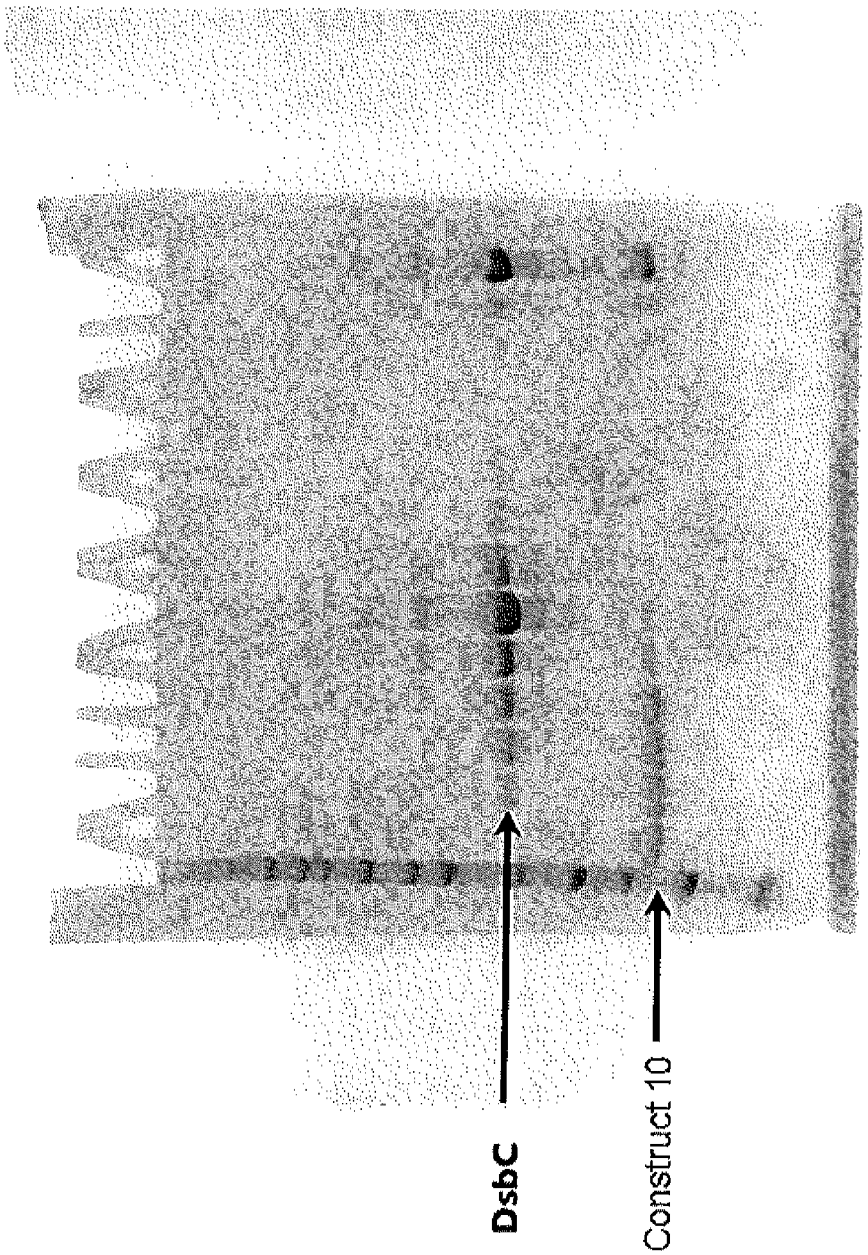
FIG. 13 illustrates a SDS-PAGE gel for the post-cleavage affinity column purification of Construct 10. The band labeled as DsbC corresponds to disulphide bond isomerase C.

A representative SDS-PAGE analysis of postcleavage affinity column purification of Construct 10 is illustrated in FIG. 13. The gel indicated a successful homogeneous production of c-heme thioether linked Construct 10.

In FIG. 14, the sequences of Constructs 7 and 10 are compared, with the c-type binding motif CXXXCH underlined.

Construct 7 was expressed in the cytoplasm and bound two heme-b units, with a net charge of −16 and pI value of 4.47. Construct 10 was expressed in the periplasm and should bind one heme-c unit and one heme-b unit, with a net charge of −17 and a pI value of 4.40. In FIG. 15 the location of CXXCH insert in the helical domain of Construct 10 is illustrated.

In one aspect, the design strategy for generating Construct 10 from Construct 7 comprised identifying proteins in which a c-type heme unit is bound to a helix and obtain consensus motif, taking into account the helical propensity of residues.

Example 15

Characterization of Construct 10

Potentiometric titration of Construct 10 was typical, as illustrated in FIG. 16, with an expected slightly more positive midpoint potential compared to the b-type peptide, $E_m$-232 mV at pH 9. Singular spectra are typical of a c-type cytochrome, suggesting that singular redox titration binds $O_2$.

Figure 17:
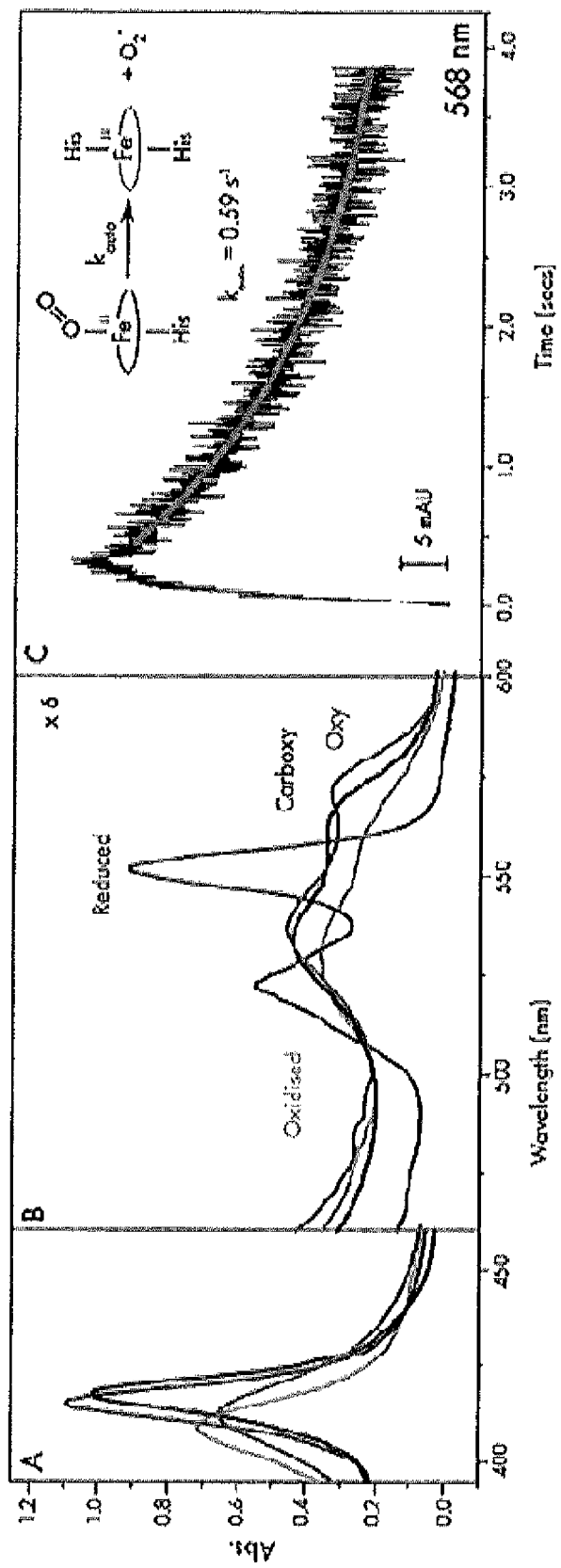
FIG. 17, comprising

Like ferrous Construct 7 and Construct 6, fully matured ferrous Construct 10 also bound molecular oxygen (FIG. 17). When titrated with iron(III) protoporphyrin IX, the c-type incorporating Construct 10 bound an additional one equivalent of heme, suggesting that the binding of a c-type heme covalently at the more C-terminal heme site returned typical two-heme binding properties.

Figure 18:
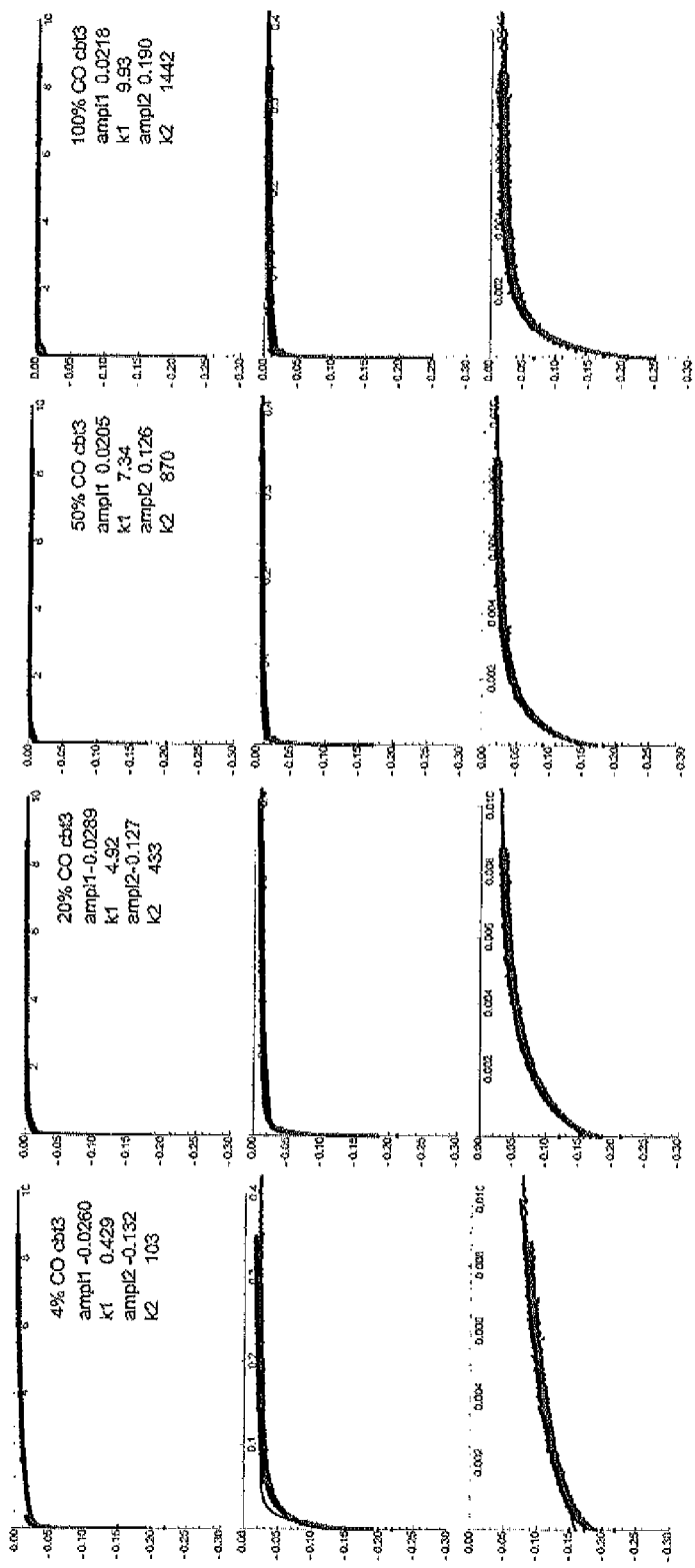
FIG. 18 illustrates the binding of CO ligand to Construct 10.

Construct 10 demonstrated similar CO ligand dynamics to those observed for Constructs 6 and 7 with other hemes (FIG. 18).

Example 16

Amphiphilic Construct for Incorporation in the Membrane of Vesicles

The $O_2$-transporting constructs described herein may be modified to have the capability of incorporating into the membranes of a cell-like vesicle. This would allow the resulting constructs to be used in a non-antigenically active $O_2$ binding protein delivery system. In such constructs, the $O_2$ binding site faces the interior of this vesicle and is thus protected from outside molecules and is maintained reduced there.

Figure 19:
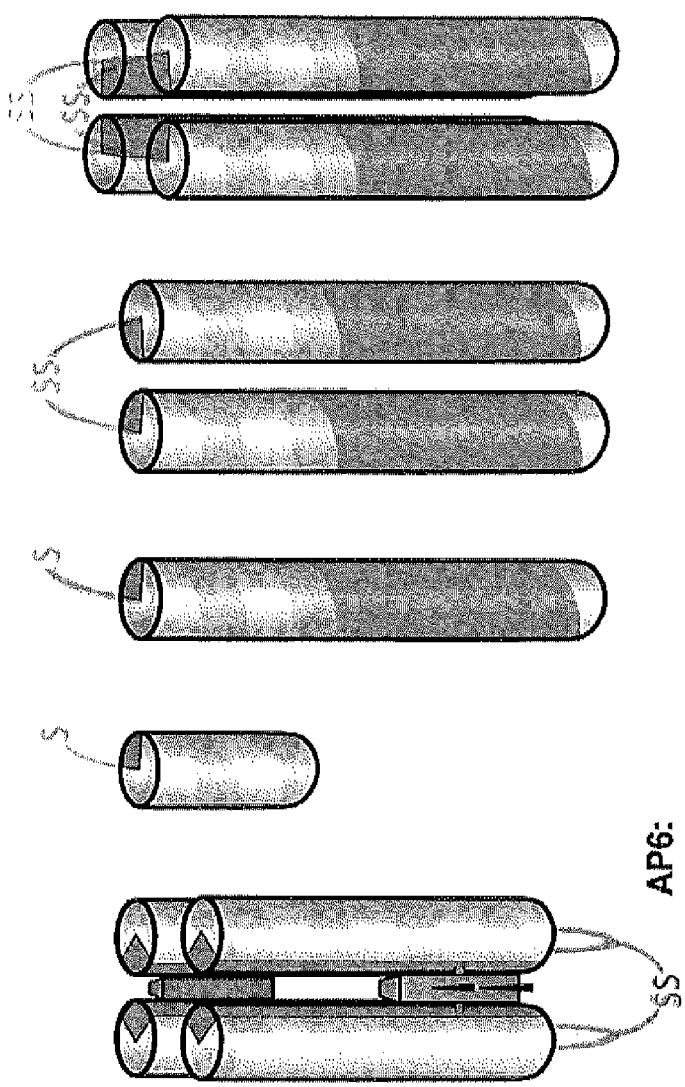
FIG. 19 illustrates the amino acid sequence of the amphiphilic construct AP6 (which corresponds to SEQ ID NO:17).

FIG. 19 illustrates a non-limiting example of an amphiphilic construct of the invention (AP6; Construct 12). Construct 12 is a tetramer sequence construct, using the water soluble portion of Constructs 6 and 7, which comprises the heme and binds $O_2$.

Figure 20:
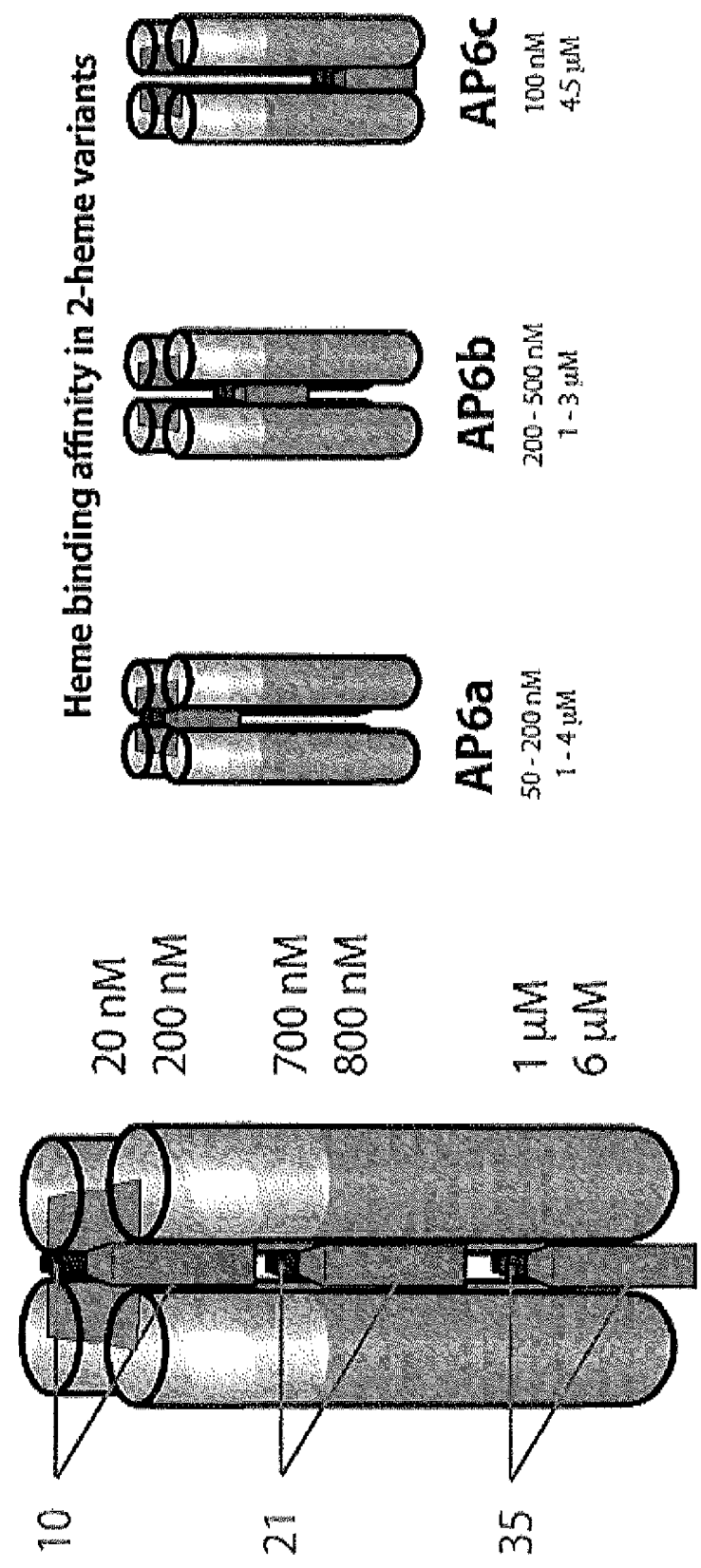
FIG. 20 illustrates the sites for Heme binding in AP6 and the corresponding binding constants (left side) and the heme binding affinities in the two-heme variants AP6a, AP6b and AP6c (right side).

Construct 12 binds to the home molecule through histidine residues at positions 10, 21 and 35 of each helix. Heme binding for each set of histidines was measured and is illustrated in FIG. 20A. The binding constants for heme binding were 20 nM, 200 nM, 700 nM, 800 nM, 1 μM and 6 μM. Site-specific mutants of AP6, wherein pairs of histidine residues were replaced with phenylalanine residues, were prepared and their affinities for heme were measured, as shown in FIG. 20B. The constructs were AP6a (Construct 13, wherein pairs of histidine residues at positions 21 and 35 were mutated to phenylalanine residues), AP6b (Construct 14, wherein pairs of histidine residues at positions 10 and 35 were mutated to phenylalanine residues) and AP6c (Construct 15, wherein pairs of histidine residues at positions 10 and 21 were mutated to phenylalanine residues). The heme binding affinities measured in these two-heme variants were 50-200 nM and 1-4 μM for AP6a, 200-500 nM and 1-3 μM for AP6b, and 100 nM and 4.5 μM for AP6c.

Figure 21:
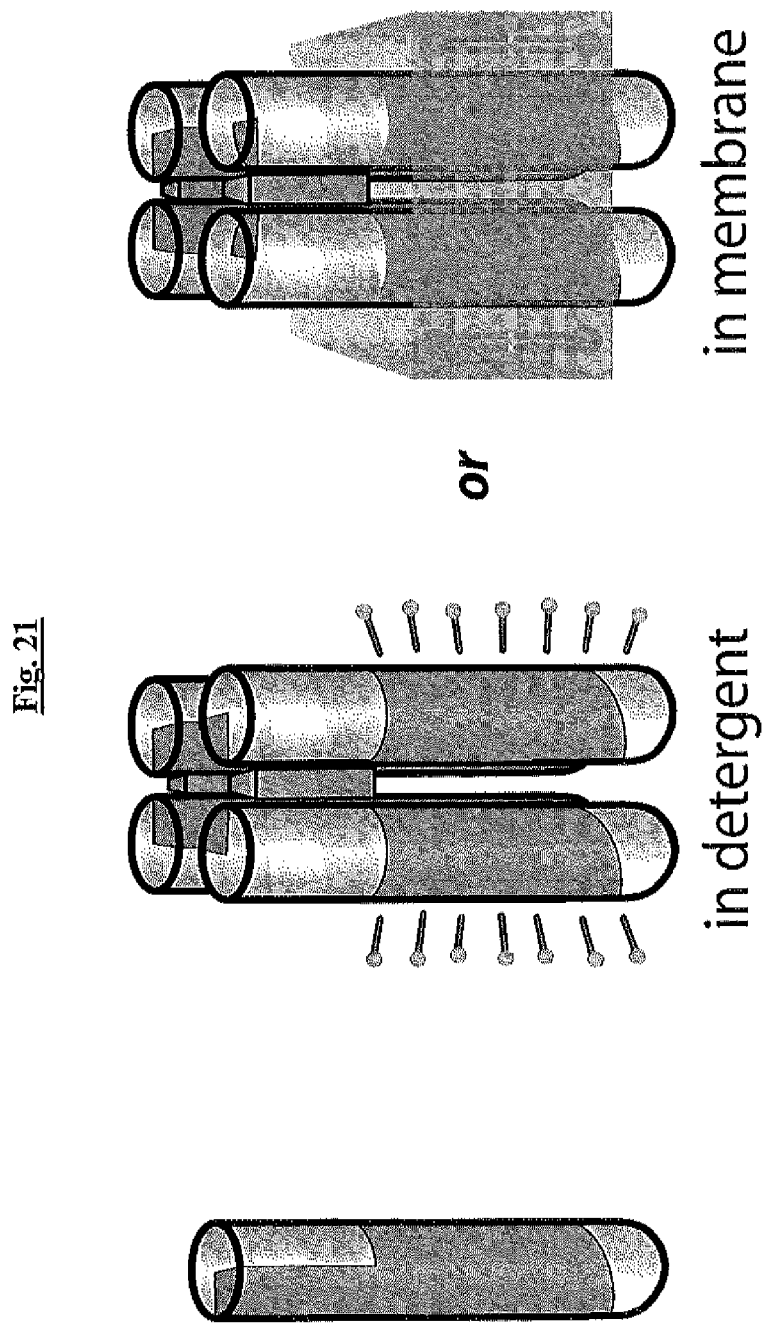
FIG. 21 illustrates the positioning of amphiphilic construct in detergent or in a membrane.
Figure 22:
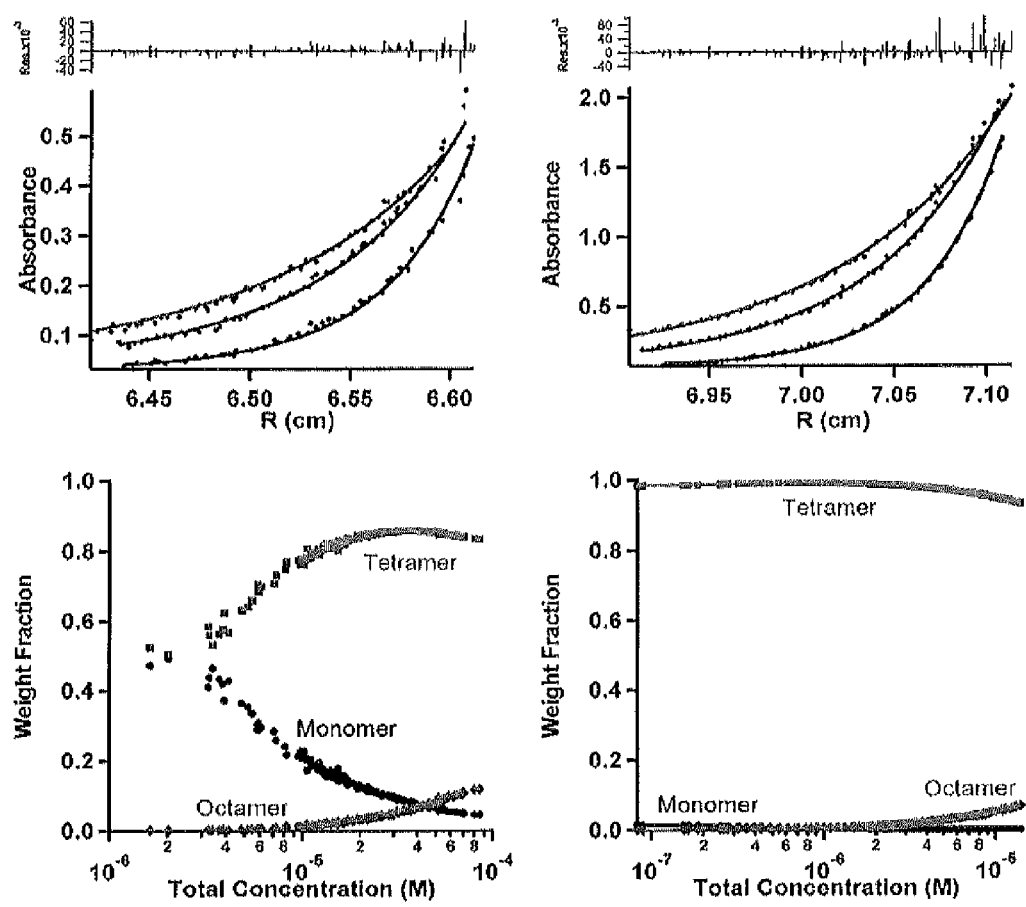
FIG. 22 illustrates the analytic ultracentrifugation data for AP6.

FIG. 21 illustrates how Construct 12 may position itself within detergent or membranes. Analytic ultracentrifugation indicated that Construct 12 aggregates as a four-helix bundle (FIG. 22).

Figure 23:
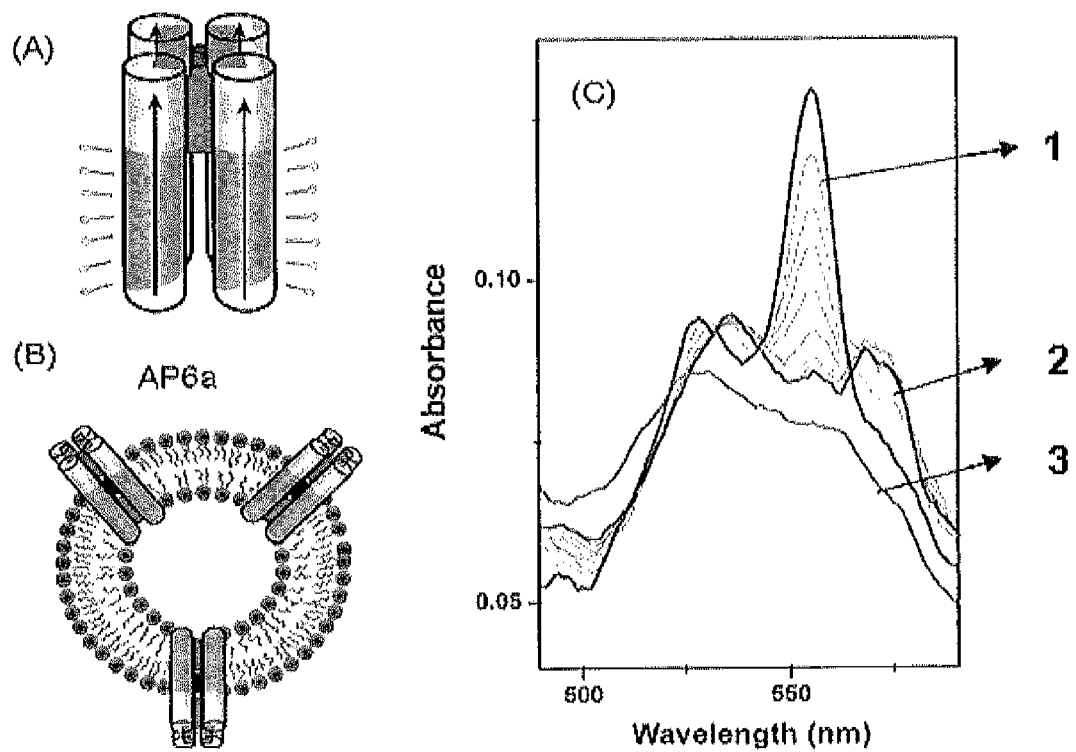
FIG. 23, comprising

The UV-vis spectra for Construct 13 (FIG. 23C) indicate that that construct is able to bind $O_2$. Curve (1) corresponds to ferrous heme (no $O_2$), curve (2) corresponds to ferrous heme ($O_2$ state), and curve (3) corresponds to ferric heme (no $O_2$).

REFERENCES

[1] Darwin, C., 1872, "Origin of Species by Means of Natural Selection, or the Preservation of Favoured Races in the Struggle for Life", 6th ed. (Murray).
[2] Muller, H. J., 1964, "The relation of recombination to mutational advance", Mutat. Res. 1, 2-9.
[3] Csete, M. E. & Doyle, J. C., 2002, "Reverse engineering of biological complexity", Science 295, 1664-1669.
[4] Kraut, D. A., Carroll, K. S. & Herschlag, D., "Challenges in enzyme mechanism and energetics", Annu. Rev. Biochem. 72, 517-571.
[5] Bolon, D. N. & Mayo, S. L., 2001, "Enzyme-like proteins by computational design", Proc. Natl. Acad. Sci. USA 98, 14274-14279.
[6] Jiang, L. et al., 2008, "De novo computational design of retro-aldol enzymes", Science 319, 1387-1391.
[7] Rothlisberger, D. et al., 2008, "Kemp elimination catalysts by computational enzyme design", Nature 453, 190-195.
[8] Kaplan, J. & DeGrado, W. F., 2004, "De novo design of catalytic proteins", Proc. Natl. Acad. Sci. USA 101, 11566-11570.
[9] Moffet, D. A. et al., 2000, "Peroxidase activity in heme proteins derived from a designed combinatorial library", J. Am. Chem. Soc. 122, 7612-7613.
[10] Monien, B. H. et al., 2007, "Detection of heme oxygenase activity in a library of four-helix bundle proteins: towards the de novo synthesis of functional heme proteins", J. Mol. Biol. 371, 739-753.
[11] Collman, J. P., Boulatov, R., Sunderland, C. J. & Fu, L., 2004, "Functional analogues of cytochrome c oxidase, myoglobin, and hemoglobin", Chem. Rev. 104, 561-588.
[12] Jencks, W. P., 1975, "Binding-energy, specificity, and enzymic catalysis—circe effect", Adv. Enzymol. 43, 219-410.
[13] Chou, P. Y. & Fasman, G. D., 1978, "Empirical predictions of protein conformation", Annu. Rev. Biochem. 47, 251-276.
[14] Regan, L. & Degrado, W. F., 1988, "Characterization of a helical protein designed from 1st principles", Science 241, 976-978.
[15] Robertson, D. E. et al. 1994, "Design and synthesis of multi-heme proteins", Nature 368, 425-431.
[16] Gibney, B. R. et al., 1999, "Iterative protein redesign", J. Am. Chem. Soc. 121, 4952-4960.
[17] Huang, S. S. et al., 2003, "X-ray structure of a maquette scaffold", J. Mol. Biol. 326, 1219-1225.
[18] Huang, S. S. et al., 2004, "The HP-1 maquette: from an apoprotein structure to a structured hemoprotein designed to promote redox-coupled proton exchange", Proc. Natl. Acad. Sci. USA 101, 5536-5541.
[19] Marshall, S. A. & Mayo, S. L., 2001, "Achieving stability and conformational specificity in designed proteins via binary patterning", J. Mol. Biol. 305, 619-631.

[20] Vallee, B. L. & Williams, R. J. P., 1968, "Metalloenzymes—entatic nature of their active sites", Proc. Natl. Acad. Sci. USA 59, 498-505.

[21] Shifman, J. M. et al., 1998, "Functionalized de novo designed proteins: mechanism of proton coupling to oxidation/reduction in heme protein maquettes", Biochemistry 37, 16815-16827.

[22] Koder, R. L. et al., 2006, "Native-like structure in designed four helix bundles driven by buried polar interactions", J. Am. Chem. Soc. 128, 14450-14451.

[23] Isogai, Y. et al., 1999, "Design and synthesis of a globin fold", Biochemistry 38, 7431-7443.

[24] Gibney, B. R. et al., 2000, "Self-assembly of heme A and heme B in a designed four-helix bundle: implications for a cytochrome c oxidase maquette", Biochemistry 39, 11041-11049.

[25] Zhuang, J. Y. et al., 2004, "Design of a five-coordinate heme protein maquette: a spectroscopic model of deoxymyoglobin", Inorg. Chem. 43, 8218-8220.

[26] Chance, B., Saronio, C. & Leigh, J. S., 1975, "Functional intermediates in reaction of cytochrome-oxidase with oxygen" Proc. Natl. Acad. Sci. USA 72, 1635-1640.

[27] Shikama, K., 1998, "The molecular mechanism of autoxidation for myoglobin and hemoglobin: a venerable puzzle", Chem. Rev. 98, 1357-1373.

[28] Wang, J. H., 1958, "Hemoglobin studies. 2. A synthetic material with hemoglobin-like property", J. Am. Chem. Soc. 80, 3168-3169.

[29] Grosset, A. M. et al., 2001, "Proof of principle in a de novo designed protein maquette: an allosterically regulated, charge-activated conformational switch in a tetra-alphahelix bundle", Biochemistry 40, 5474-5487.

[30] Trent, J. T., Hvitved, A. N. & Hargrove, M. S., 2001, "A model for ligand binding to hexacoordinate hemoglobins", Biochemistry 40, 6155-6163.

[31] Dewilde, S. et al., 2001, "Biochemical characterization and ligand binding properties of neuroglobin, a novel member of the globin family", J. Biol. Chem. 276, 38949-38955.

[32] Pesce, A. et al., 2003, "Human brain neuroglobin structure reveals a distinct mode of controlling oxygen affinity", Structure 11, 1087-1095.

[33] Peterson, E. S. et al., 1997, "A comparison of functional and structural consequences of the tyrosine B10 and glutamine E7 motifs in two invertebrate hemoglobins (*Ascaris suum* and *Lucina pectinata*)", Biochemistry 36, 13110-13121.

[34] Borovik, A. S., 2005, "Bioinspired hydrogen bond motifs in ligand design: the role of noncovalent interactions in metal ion mediated activation of dioxygen", Acc. Chem. Res. 38, 54-61.

[35] Mclendon, G., 1991, "Control of biological electron-transport via molecular recognition and binding—the velcro model", Struct. Bond. 75, 159-174.

[36] Page, C. C., Moser, C. C. & Dutton, P. L., 2003, "Mechanism for electron transfer within and between proteins", Curr. Opin. Chem. Biol. 7, 551-556.

[37] Brannigan, J. A. & Wilkinson, A. J., 2002, "Protein engineering 20 years on", Nature Rev. Mol. Cell. Biol. 3, 964-970.

[38] Hilvert, D., 2000, "Critical analysis of antibody catalysis", Annu. Rev. Biochem. 69, 751-793.

[39] Carbone, M. N. & Arnold, F. H., 2007, "Engineering by homologous recombination: exploring sequence and function within a conserved fold", Curr. Opin. Struct. Biol. 17, 454-459.

[40] Moser, C. C. et al., 1992, "Nature of biological electron-transfer", Nature 355, 796-802.

[41] Benkovic, S. J. & Hammes-Schiffer, S., 2003, "A perspective on enzyme catalysis", Science 301, 1196-1202.

[42] Warshel, A., 2003, "Computer simulations of enzyme catalysis: methods, progress, and insights", Annu. Rev. Biophys. Biomol. Struct. 32, 425-443.

[43] Frauenfelder, H., McMahon, B. H. & Fenimore, P. W., 2003, "Myoglobin: the hydrogen atom of biology and a paradigm of complexity", Proc. Natl. Acad. Sci. USA 100, 8615-8617.

[44] Moffet, D. A. et al., 2001, "Carbon monoxide binding by de novo heme proteins derived from designed combinatorial libraries", J. Am. Chem. Soc. 123, 2109-2115.

[45] Hargrove, M. S., 2000, "A flash photolysis method to characterize hexacoordinate hemoglobin kinetics", Biophys. J. 79, 2733-2738.

[46] Ansari, A. et al., 1992, "The role of solvent viscosity in the dynamics of protein conformational-changes", Science 256, 1796-1798.

[47] Springer, B. A., Sligar, S. G., Olson, J. S. & Phillips, G. N., 1994, "Mechanisms of ligand recognition in myoglobin", Chem. Rev. 94, 699-714.

[48] Mathews, A. J. et al., 1989, "The effects of E7 and E11 mutations on the kinetics of ligand binding to R-state human-hemoglobin", J. Biol. Chem. 264, 16573-16583.

[49] Goldberg, D. E., 1999, "Oxygen-avid hemoglobin of *Ascaris*", Chem. Rev. 99, 3371-3378.

[50] Sharma, V. S., Schmidt, M. R. & Ranney, H. M., 1976, "Dissociation of CO from carboxyhemoglobin", J. Biol. Chem. 251, 4267-4272.

[51] Smith, K. M., Parish, D. W. & Inouye, W. S., 1986, "Methyl deuteration reactions in vinylporphyrins: protoporphyrins IX, 111, and X111", J. Org. Chem. 51, 666-671.

[52] Engels, W. R., 1993, "Contributing software to the internet: the amplify program", Trends Biochem. Sci. 18, 448-450.

[53] Stemmer, W. P. C., Crameri, A., Ha, K. D., Brennan, T. M. Heyneker, H. L., 1995, "Single step assembly of a gene and entire plasmid from large numbers of oligodeoxyribonucleotides", Gene 164, 49-53.

[54] Moore, J. T., Uppal, A., Maley, F. & Maley, G. F., 1993, "Overcoming inclusion body formation in a high-level expression system", Protein Expr. Purif. 4, 160-163.

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed:

1. A composition comprising a peptide comprising an amino acid sequence selected from the group consisting of
SEQ ID NO:1, the cystine derivative of SEQ ID NO:1,
(SEQ ID NO:2)-LOOP-(SEQ ID NO:2),
(SEQ ID NO:21)-LOOP-(SEQ ID NO:22)-LOOP-(SEQ ID NO:22)-LOOP-(SEQ ID NO:22),
(SEQ ID NO:22)-LOOP-(SEQ ID NO:22)-LOOP-(SEQ ID NO:22)-LOOP-(SEQ ID NO:22),
(SEQ ID NO:21)-LOOP-(SEQ ID NO:23)-LOOP-(SEQ ID NO:22)-LOOP-(SEQ ID NO:22),
(SEQ ID NO:21)-LOOP-(SEQ ID NO:22)-LOOP-(SEQ ID NO:22)-LOOP-(SEQ ID NO:24),
SEQ ID NO:17, the homodimer of the cystine derivative of SEQ ID NO:17,
SEQ ID NO:18, the homodimer of the cystine derivative of SEQ ID NO:18,
SEQ ID NO:19, the homodimer of the cystine derivative of SEQ ID NO:19,
SEQ ID NO:20, and the homodimer of the cystine derivative of SEQ ID NO:20.

2. The composition of claim 1, wherein each occurrence of LOOP is independently selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGSGCGSGG (SEQ ID NO:27).

3. The composition of claim 2, wherein said peptide comprises an amino acid sequence selected from the group consisting of (SEQ ID NO:2)-(SEQ ID NO:3)-(SEQ ID NO:2), (SEQ ID NO:2)-(SEQ ID NO:4)-(SEQ ID NO:2), SEQ ID NO:11, SEQ ID NO:12, SEQ ID NO:13, SEQ ID NO:14 and SEQ ID NO:15.

4. The composition of claim 1, further comprising at least one heme;
wherein said peptide is bound to said at least one heme.

5. The composition of claim 4, wherein said at least one heme is selected from the group consisting of heme A, heme B, heme C, heme O, mesohemes, deuterohemes, synthetic dicyano porphyrins and symmetrical porphyrins.

6. A method of removing oxygen gas from an oxygen gas-containing atmosphere, wherein said method comprises exposing to said oxygen gas-containing atmosphere a composition comprising:
at least one heme; and
a peptide comprising an amino acid sequence selected from the group consisting of SEQ ID NO:1, the cystine derivative of SEQ ID NO:1, (SEQ ID NO:2)-LOOP-(SEQ ID NO:2), (SEQ ID NO:22)-LOOP-(SEQ ID NO:22)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:22), (SEQ ID NO:21)-LOOP-(SEQ ID NO:23)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:24), SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20,
wherein said at least one heme is bound to said peptide.

7. The method of claim 6, wherein said at least one heme is selected from the group consisting of heme A, heme B, heme C, heme O, mesohemes, deuterohemes, synthetic dicyano porphyrins and symmetrical porphyrins.

8. The method of claim 6, wherein each occurrence of LOOP is independently selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGSGCGSGG (SEQ ID NO:27).

9. The method of claim 8, wherein said peptide comprises an amino acid sequence selected from the group consisting of (SEQ ID NO:2)-(SEQ ID NO:3)-(SEQ ID NO:2), (SEQ ID NO:2)-(SEQ ID NO:4)-(SEQ ID NO:2), SEQ ID NO:11, SEQ ID NO:12, SEQ ID NO:13, SEQ ID NO:14 and SEQ ID NO:15.

10. A method of treating an oxygen transport deficiency in a mammal in need thereof, wherein said method comprises administering to said mammal an effective amount of a composition comprising:
   at least one heme; and
   a peptide comprising an amino acid sequence selected from the group consisting of SEQ ID NO:1, the cystine derivative of SEQ ID NO:1, (SEQ ID NO:2)-LOOP-(SEQ ID NO:2), (SEQ ID NO:22)-LOOP-(SEQ ID NO:22)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:22), (SEQ ID NO:21)-LOOP-(SEQ ID NO:23)-LOOP-(SEQ ID NO:22)-LOOP-(SEQ ID NO:22), (SEQ ID NO:21)-LOOP-(SEQ ID NO:22)-LOOP-(SEQ ID NO:22)-LOOP-(SEQ ID NO:24), SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20,
      wherein said at least one heme is bound to said peptide.

11. The method of claim 10, wherein said at least one heme is selected from the group consisting of heme A, heme B, heme C, heme O, mesohemes, deuterohemes, synthetic dicyano porphyrins and symmetrical porphyrins.

12. The method of claim 10, wherein each occurrence of LOOP is independently selected from the group consisting of GGSGSGSG (SEQ ID NO:3), GGSGGGSG (SEQ ID NO:4), GGSGSGSGG (SEQ ID NO:25), GGSGGSGGSGG (SEQ ID NO:26) and GGSGCGSGG (SEQ ID NO:27).

13. The method of claim 12, wherein said peptide comprises an amino acid sequence selected from the group consisting of (SEQ ID NO:2)-(SEQ ID NO:3)-(SEQ ID NO:2), (SEQ ID NO:2)-(SEQ ID NO:4)-(SEQ ID NO:2), SEQ ID NO:11, SEQ ID NO:12, SEQ ID NO:13, SEQ ID NO:14 and SEQ ID NO:15.

14. The method of claim 10, wherein said oxygen transport deficiency is selected from the group consisting of chronic anemia, acute anemia, sickle cell anemia, anemia associated with cancer, anemia associated with cancer chemotherapy, and anemia associated with use of radiation for cancer treatment.

15. The composition of claim 1, further comprising a vesicle, wherein said vesicle comprises:
   an amphiphilic material which is selected from the group consisting of a detergent, a phospholipid, and a combination thereof;
   said at least one heme; and
   said peptide,
      wherein said peptide is selected from the group consisting of SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20, and,
      wherein said peptide is incorporated in the walls of said vesicle and said peptide is bound to said at least one heme.

16. A method of treating an oxygen transport deficiency in a mammal in need thereof, wherein said method comprises administering to said mammal an effective amount of a composition comprising a vesicle, wherein said vesicle comprises:
   an amphiphilic material which is selected from the group consisting of a detergent, a phospholipid, and a combination thereof;
   at least one heme; and
   a peptide comprising an amino acid sequence selected from the group consisting of SEQ ID NO:17, the homodimer of the cystine derivative of SEQ ID NO:17, SEQ ID NO:18, the homodimer of the cystine derivative of SEQ ID NO:18, SEQ ID NO:19, the homodimer of the cystine derivative of SEQ ID NO:19, SEQ ID NO:20, and the homodimer of the cystine derivative of SEQ ID NO:20,
      wherein said peptide is incorporated in the walls of said vesicle and said peptide is bound at said at least one heme.

17. The method of claim 16, wherein said at least one heme is selected from the group consisting of heme A, heme B, heme C, heme O, mesohemes, deuterohemes, synthetic dicyano porphyrins and symmetrical porphyrins.

18. The method of claim 16, wherein said oxygen transport deficiency is selected from the group consisting of chronic anemia, acute anemia, sickle cell anemia, anemia associated with cancer, anemia associated with cancer chemotherapy, and anemia associated with use of radiation for cancer treatment.

19. The method of claim 18, wherein said mammal is human.

* * * * *

SEQUENCE LISTING

<160> NUMBER OF SEQ ID NOS: 29

<210> SEQ ID NO 1
<211> LENGTH: 62
<212> TYPE: PRT
<213> ORGANISM: Artificial Sequence
<220> FEATURE:
<223> OTHER INFORMATION: chemically synthesized

<400> SEQUENCE: 1

Gly Glu Ile Trp Lys Gln His Glu Asp Ala Leu Gln Lys Phe Glu Glu
1               5                   10                  15

Ala Leu Asn Gln Phe Glu Asp Leu Lys Gln Leu Gly Gly Ser Gly Cys
            20                  25                  30

Gly Ser Gly Gly Glu Ile Trp Lys Gln His Glu Asp Ala Leu Gln Lys
        35                  40                  45

Phe Glu Glu Ala Leu Asn Gln Phe Glu Asp Leu Lys Gln Leu
    50                  55                  60

<210> SEQ ID NO 2
<211> LENGTH: 27
<212> TYPE: PRT
<213> ORGANISM: Artificial Sequence
<220> FEATURE:
<223> OTHER INFORMATION: chemically synthesized

<400> SEQUENCE: 2

Gly Glu Ile Trp Lys Gln His Glu Asp Ala Leu Gln Lys Phe Glu Glu
1               5                   10                  15

Ala Leu Asn Gln Phe Glu Asp Leu Lys Gln Leu
            20                  25

<210> SEQ ID NO 3
<211> LENGTH: 8
<212> TYPE: PRT
<213> ORGANISM: Artificial Sequence
<220> FEATURE:
<223> OTHER INFORMATION: chemically synthesized

<400> SEQUENCE: 3

Gly Gly Ser Gly Ser Gly Ser Gly
1               5

<210> SEQ ID NO 4
<211> LENGTH: 8
<212> TYPE: PRT
<213> ORGANISM: Artificial Sequence
<220> FEATURE:
<223> OTHER INFORMATION: chemically synthesized

<400> SEQUENCE: 4

Gly Gly Ser Gly Gly Gly Ser Gly
1               5

<210> SEQ ID NO 5
<211> LENGTH: 27
<212> TYPE: PRT
<213> ORGANISM: Artificial Sequence
<220> FEATURE:
<223> OTHER INFORMATION: chemically synthesized

```
<400> SEQUENCE: 5

Glu Leu Leu Lys Leu Leu Glu Glu Leu Lys Lys Leu Glu Glu Leu
1               5                   10                  15

Leu Lys Leu Leu Glu Glu Leu Leu Lys Lys Leu
            20                  25

<210> SEQ ID NO 6
<211> LENGTH: 31
<212> TYPE: PRT
<213> ORGANISM: Artificial Sequence
<220> FEATURE:
<223> OTHER INFORMATION: chemically synthesized

<400> SEQUENCE: 6

Cys Gly Gly Gly Glu Leu Trp Lys Leu His Glu Glu Leu Lys Lys
1               5                   10                  15

Phe Glu Glu Leu Leu Lys Leu His Glu Glu Arg Leu Lys Lys Leu
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: chemically synthesized

<400> SEQUENCE: 7

Cys Gly Gly Gly Glu Ile Trp Lys Leu His Glu Glu Phe Leu Lys Lys
1               5                   10                  15

Phe Glu Glu Leu Leu Lys Leu His Glu Glu Arg Leu Lys Lys Leu
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: chemically synthesized

<400> SEQUENCE: 8

Cys Gly Gly Gly Glu Ile Trp Lys Gln His Glu Glu Ala Leu Lys Lys
1               5                   10                  15

Phe Glu Glu Ala Leu Lys Gln Phe Glu Glu Leu Lys Lys Leu
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: chemically synthesized

<400> SEQUENCE: 9

Cys Gly Gly Gly Glu Ile Trp Lys Gln His Glu Asp Ala Leu Gln Lys
1               5                   10                  15

Phe Glu Asp Ala Leu Asn Gln Phe Glu Glu Leu Lys Gln Leu
            20                  25                  30

<210> SEQ ID NO 10
<211> LENGTH: 14
<212> TYPE: PRT
<213> ORGANISM: Artificial Sequence
<220> FEATURE:
<223> OTHER INFORMATION: chemically synthesized
```

```
<400> SEQUENCE: 10

Leu Glu Glu Leu Leu Lys Lys Leu Glu Leu Leu Lys Leu
1               5                   10

<210> SEQ ID NO 11
<211> LENGTH: 138
<212> TYPE: PRT
<213> ORGANISM: Artificial Sequence
<220> FEATURE:
<223> OTHER INFORMATION: chemically synthesized

<400> SEQUENCE: 11

Gly Met Thr Pro Glu Gln Ile Trp Lys Gln His Glu Asp Ala Leu Gln
1               5                   10                  15

Lys Phe Glu Asp Ala Leu Asn Gln Phe Glu Glu Leu Lys Gln Leu Gly
                20                  25                  30

Gly Ser Gly Ser Gly Ser Gly Gly Glu Ile Trp Lys Gln His Glu Asp
            35                  40                  45

Ala Leu Gln Lys Phe Glu Asp Ala Leu Asn Gln Phe Glu Glu Leu Lys
        50                  55                  60

Gln Leu Gly Gly Ser Gly Ser Gly Ser Gly Gly Glu Ile Trp
65                  70                  75                  80

Lys Gln His Glu Asp Ala Leu Gln Lys Phe Glu Asp Ala Leu Asn Gln
                85                  90                  95

Phe Glu Glu Leu Lys Gln Leu Gly Gly Ser Gly Ser Gly Ser Gly Gly
                100                 105                 110

Glu Ile Trp Lys Gln His Glu Asp Ala Leu Gln Lys Phe Glu Asp Ala
            115                 120                 125

Leu Asn Gln Phe Glu Glu Leu Lys Gln Leu
        130                 135

<210> SEQ ID NO 12
<211> LENGTH: 136
<212> TYPE: PRT
<213> ORGANISM: Artificial Sequence
<220> FEATURE:
<223> OTHER INFORMATION: chemically synthesized

<400> SEQUENCE: 12

Gly Met Thr Pro Glu Gln Ile Trp Lys Gln His Glu Asp Ala Leu Gln
1               5                   10                  15

Lys Phe Glu Asp Ala Leu Asn Gln Phe Glu Glu Leu Lys Gln Leu Gly
                20                  25                  30

Gly Ser Gly Ser Gly Ser Gly Gly Glu Ile Trp Lys Gln His Glu Asp
            35                  40                  45

Ala Leu Gln Lys Phe Glu Asp Ala Leu Asn Gln Phe Glu Glu Leu Lys
        50                  55                  60

Gln Leu Gly Gly Ser Gly Ser Gly Ser Gly Gly Glu Ile Trp Lys Gln
65                  70                  75                  80

His Glu Asp Ala Leu Gln Lys Phe Glu Asp Ala Leu Asn Gln Phe Glu
                85                  90                  95

Glu Leu Lys Gln Leu Gly Gly Ser Gly Ser Gly Ser Gly Gly Glu Ile
                100                 105                 110

Trp Lys Gln His Glu Asp Ala Leu Gln Lys Phe Glu Asp Ala Leu Asn
            115                 120                 125

Gln Phe Glu Glu Leu Lys Gln Leu
        130                 135
```

```
<210> SEQ ID NO 13
<211> LENGTH: 132
<212> TYPE: PRT
<213> ORGANISM: Artificial Sequence
<220> FEATURE:
<223> OTHER INFORMATION: chemically synthesized

<400> SEQUENCE: 13

Gly Glu Ile Trp Lys Gln His Glu Asp Ala Leu Gln Lys Phe Glu Asp
1               5                   10                  15

Ala Leu Asn Gln Phe Glu Glu Leu Lys Gln Leu Gly Gly Ser Gly Ser
            20                  25                  30

Gly Ser Gly Gly Glu Ile Trp Lys Gln His Glu Asp Ala Leu Gln Lys
        35                  40                  45

Phe Glu Asp Ala Leu Asn Gln Phe Glu Glu Leu Lys Gln Leu Gly Gly
    50                  55                  60

Ser Gly Ser Gly Ser Gly Gly Glu Ile Trp Lys Gln His Glu Asp Ala
65                  70                  75                  80

Leu Gln Lys Phe Glu Asp Ala Leu Asn Gln Phe Glu Glu Leu Lys Gln
                85                  90                  95

Leu Gly Gly Ser Gly Ser Gly Ser Gly Gly Glu Ile Trp Lys Gln His
            100                 105                 110

Glu Asp Ala Leu Gln Lys Phe Glu Asp Ala Leu Asn Gln Phe Glu Glu
        115                 120                 125

Leu Lys Gln Leu
    130

<210> SEQ ID NO 14
<211> LENGTH: 138
<212> TYPE: PRT
<213> ORGANISM: Artificial Sequence
<220> FEATURE:
<223> OTHER INFORMATION: chemically synthesized

<400> SEQUENCE: 14

Gly Met Thr Pro Glu Gln Ile Trp Lys Gln His Glu Asp Ala Leu Gln
1               5                   10                  15

Lys Phe Glu Asp Ala Leu Asn Gln Phe Glu Glu Leu Lys Gln Leu Gly
            20                  25                  30

Gly Ser Gly Ser Gly Ser Gly Gly Glu Ile Cys Lys Cys His Glu Asp
        35                  40                  45

Ala Leu Gln Lys Phe Glu Asp Ala Leu Asn Gln Phe Glu Glu Leu Lys
    50                  55                  60

Gln Leu Gly Gly Ser Gly Gly Ser Gly Gly Ser Gly Gly Glu Ile Trp
65                  70                  75                  80

Lys Gln His Glu Asp Ala Leu Gln Lys Phe Glu Asp Ala Leu Asn Gln
                85                  90                  95

Phe Glu Glu Leu Lys Gln Leu Gly Gly Ser Gly Ser Gly Ser Gly Gly
            100                 105                 110

Glu Ile Trp Lys Gln His Glu Asp Ala Leu Gln Lys Phe Glu Asp Ala
        115                 120                 125

Leu Asn Gln Phe Glu Glu Leu Lys Gln Leu
    130                 135

<210> SEQ ID NO 15
<211> LENGTH: 136
<212> TYPE: PRT
<213> ORGANISM: Artificial Sequence
```

```
<220> FEATURE:
<223> OTHER INFORMATION: chemically synthesized
<220> FEATURE:
<221> NAME/KEY: MOD_RES
<222> LOCATION: (136)..(136)
<223> OTHER INFORMATION: leucinamide

<400> SEQUENCE: 15

Met Thr Pro Glu Gln Ile Trp Lys Gln His Glu Asp Ala Leu Gln Lys
1               5                   10                  15

Phe Glu Asp Ala Leu Asn Gln Phe Glu Leu Lys Gln Leu Gly Gly
            20                  25                  30

Ser Gly Ser Gly Ser Gly Gly Glu Ile Trp Lys Gln His Glu Asp Ala
        35                  40                  45

Leu Gln Lys Phe Glu Asp Ala Leu Asn Gln Phe Glu Glu Leu Lys Gln
    50                  55                  60

Leu Gly Gly Ser Gly Gly Ser Gly Gly Ser Gly Glu Ile Trp Lys
65                  70                  75                  80

Gln His Glu Asp Ala Leu Gln Lys Phe Glu Asp Ala Leu Asn Gln Phe
                85                  90                  95

Glu Glu Leu Lys Gln Leu Gly Gly Ser Gly Cys Gly Ser Gly Gly Glu
            100                 105                 110

Ile Trp Lys Gln His Glu Asp Ala Leu Gln Lys Phe Glu Ala Leu Gln
        115                 120                 125

Phe Glu Glu Asp Leu Lys Gln Xaa
    130                 135

<210> SEQ ID NO 16
<211> LENGTH: 64
<212> TYPE: PRT
<213> ORGANISM: Artificial Sequence
<220> FEATURE:
<223> OTHER INFORMATION: chemically synthesized

<400> SEQUENCE: 16

Gly Ser Pro Glu Ile Trp Lys Gln His Glu Asp Ala Leu Gln Lys Phe
1               5                   10                  15

Glu Asp Ala Leu Asn Gln Phe Glu Glu Leu Lys Gln Leu Gly Gly Ser
            20                  25                  30

Gly Cys Gly Ser Gly Gly Glu Ile Trp Lys Gln His Glu Asp Ala Leu
        35                  40                  45

Gln Lys Phe Glu Asp Ala Leu Asn Gln Phe Glu Glu Leu Lys Gln Leu
    50                  55                  60

<210> SEQ ID NO 17
<211> LENGTH: 44
<212> TYPE: PRT
<213> ORGANISM: Artificial Sequence
<220> FEATURE:
<223> OTHER INFORMATION: chemically synthesized

<400> SEQUENCE: 17

Cys Gly Gly Gly Glu Ile Trp Lys Gln His Glu Glu Ala Leu Lys Lys
1               5                   10                  15

Leu Phe Ala Phe His Phe Ile Leu Pro Phe Ile Ile Met Ala Ile Ala
            20                  25                  30

Met Val His Leu Leu Phe Leu Phe Gly Glu Gly Leu
        35                  40
```

```
<210> SEQ ID NO 18
<211> LENGTH: 44
<212> TYPE: PRT
<213> ORGANISM: Artificial Sequence
<220> FEATURE:
<223> OTHER INFORMATION: chemically synthesized

<400> SEQUENCE: 18

Cys Gly Gly Gly Glu Ile Trp Lys Gln His Glu Glu Ala Leu Lys Lys
1               5                   10                  15

Leu Phe Ala Phe Phe Phe Ile Leu Pro Phe Ile Ile Met Ala Ile Ala
            20                  25                  30

Met Val Phe Leu Leu Phe Leu Phe Gly Glu Gly Leu
        35                  40

<210> SEQ ID NO 19
<211> LENGTH: 44
<212> TYPE: PRT
<213> ORGANISM: Artificial Sequence
<220> FEATURE:
<223> OTHER INFORMATION: chemically synthesized

<400> SEQUENCE: 19

Cys Gly Gly Gly Glu Ile Trp Lys Gln Phe Glu Glu Ala Leu Lys Lys
1               5                   10                  15

Leu Phe Ala Phe His Phe Ile Leu Pro Phe Ile Ile Met Ala Ile Ala
            20                  25                  30

Met Val Phe Leu Leu Phe Leu Phe Gly Glu Gly Leu
        35                  40

<210> SEQ ID NO 20
<211> LENGTH: 44
<212> TYPE: PRT
<213> ORGANISM: Artificial Sequence
<220> FEATURE:
<223> OTHER INFORMATION: chemically synthesized

<400> SEQUENCE: 20

Cys Gly Gly Gly Glu Ile Trp Lys Gln Phe Glu Glu Ala Leu Lys Lys
1               5                   10                  15

Leu Phe Ala Phe Phe Phe Ile Leu Pro Phe Ile Ile Met Ala Ile Ala
            20                  25                  30

Met Val His Leu Leu Phe Leu Phe Gly Glu Gly Leu
        35                  40

<210> SEQ ID NO 21
<211> LENGTH: 26
<212> TYPE: PRT
<213> ORGANISM: Artificial Sequence
<220> FEATURE:
<223> OTHER INFORMATION: chemically synthesized

<400> SEQUENCE: 21

Gln Ile Trp Lys Gln His Glu Asp Ala Leu Gln Lys Phe Glu Asp Ala
1               5                   10                  15

Leu Asn Gln Phe Glu Glu Leu Lys Gln Leu
            20                  25

<210> SEQ ID NO 22
<211> LENGTH: 26
<212> TYPE: PRT
<213> ORGANISM: Artificial Sequence
<220> FEATURE:
<223> OTHER INFORMATION: chemically synthesized
```

```
<400> SEQUENCE: 22

Glu Ile Trp Lys Gln His Glu Asp Ala Leu Gln Lys Phe Glu Asp Ala
1               5                   10                  15

Leu Asn Gln Phe Glu Glu Leu Lys Gln Leu
            20                  25

<210> SEQ ID NO 23
<211> LENGTH: 26
<212> TYPE: PRT
<213> ORGANISM: Artificial Sequence
<220> FEATURE:
<223> OTHER INFORMATION: chemically synthesized

<400> SEQUENCE: 23

Glu Ile Cys Lys Cys His Glu Asp Ala Leu Gln Lys Phe Glu Asp Ala
1               5                   10                  15

Leu Asn Gln Phe Glu Glu Leu Lys Gln Leu
            20                  25

<210> SEQ ID NO 24
<211> LENGTH: 25
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (25)..(25)
<223> OTHER INFORMATION: leucinamide

<400> SEQUENCE: 24

Glu Ile Trp Lys Gln His Glu Asp Ala Leu Gln Lys Phe Glu Ala Leu
1               5                   10                  15

Gln Phe Glu Glu Asp Leu Lys Gln Xaa
            20                  25

<210> SEQ ID NO 25
<211> LENGTH: 9
<212> TYPE: PRT
<213> ORGANISM: Artificial Sequence
<220> FEATURE:
<223> OTHER INFORMATION: chemically synthesized

<400> SEQUENCE: 25

Gly Gly Ser Gly Ser Gly Ser Gly Gly
1               5

<210> SEQ ID NO 26
<211> LENGTH: 11
<212> TYPE: PRT
<213> ORGANISM: Artificial Sequence
<220> FEATURE:
<223> OTHER INFORMATION: chemically synthesized

<400> SEQUENCE: 26

Gly Gly Ser Gly Gly Ser Gly Gly Ser Gly Gly
1               5                   10

<210> SEQ ID NO 27
<211> LENGTH: 9
<212> TYPE: PRT
<213> ORGANISM: Artificial Sequence
<220> FEATURE:
<223> OTHER INFORMATION: chemically synthesized
```

```
<400> SEQUENCE: 27

Gly Gly Ser Gly Cys Gly Ser Gly Gly
1               5

<210> SEQ ID NO 28
<211> LENGTH: 12
<212> TYPE: PRT
<213> ORGANISM: Artificial Sequence
<220> FEATURE:
<223> OTHER INFORMATION: chemically synthesized

<400> SEQUENCE: 28

Glu Ile Trp Lys Gln His Glu Asp Ala Leu Gln Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: chemically synthesized

<400> SEQUENCE: 29

Glu Cys Ile Ala Cys His Glu Asp Ala Leu Gln Lys
1               5                   10
```